United States Patent
Lewis et al.

(10) Patent No.: US 11,785,877 B2
(45) Date of Patent: Oct. 17, 2023

(54) AUTOMATED SAMPLE COLLECTION AND TRACKING SYSTEM

(71) Applicant: Climate LLC, Saint Louis, MO (US)

(72) Inventors: Michael David Lewis, Hazelwood, MO (US); Shalom Friss, St. Louis, MO (US); Jyoti Dharna, Chesterfield, MO (US); Christopher P. Aulbach, Defiance, MO (US); Jason R. Sontheimer, Dardenne Prairie, MO (US); Atif Khan, Lake Saint Louis, MO (US)

(73) Assignee: CLIMATE LLC, Saint Louis, MO (US)

( * ) Notice: Subject to any disclaimer, the term of this patent is extended or adjusted under 35 U.S.C. 154(b) by 852 days.

(21) Appl. No.: 16/670,247

(22) Filed: Oct. 31, 2019

(65) Prior Publication Data

US 2020/0128721 A1 Apr. 30, 2020

Related U.S. Application Data

(60) Provisional application No. 62/753,692, filed on Oct. 31, 2018.

(51) Int. Cl.
*A01B 79/00* (2006.01)
*G01N 33/24* (2006.01)
(Continued)

(52) U.S. Cl.
CPC ............ *A01B 79/005* (2013.01); *G01N 1/02* (2013.01); *G01N 33/24* (2013.01); *G06F 3/0482* (2013.01);
(Continued)

(58) Field of Classification Search
CPC ............ G01N 1/20; G01N 1/286; G01N 1/10; G01N 1/12; G01N 1/16; G01N 1/2273;
(Continued)

(56) References Cited

U.S. PATENT DOCUMENTS

| 5,878,371 A | 3/1999 | Hale et al. |
| 2002/0022929 A1 | 2/2002 | Ell |

(Continued)

FOREIGN PATENT DOCUMENTS

| CN | 103530361 | 1/2014 |
| CN | 103793851 | 5/2014 |

(Continued)

OTHER PUBLICATIONS

International Searching Authority, "Search Report" in application No. PCT/US19/59206, dated Jan. 16, 2020, 13 pages.
(Continued)

*Primary Examiner* — Harshad R Patel
*Assistant Examiner* — Truong D Phan
(74) *Attorney, Agent, or Firm* — Harness, Dickey & Pierce, P.L.C.

(57) ABSTRACT

In an embodiment, a computer-implemented method of tracking soil sampling in a field is disclosed. The method comprises receiving, by a processor, digitally stored field map data and digitally stored sampling data. The method further comprises displaying, by the processor, a field map depicting the first set of sampling points in a computer-generated graphical user interface. In addition, the method comprises receiving a selection of a first sampling point and displaying first sampling data associated with the first sampling point. The method also comprises receiving an update indicating that a soil sample has been collected at the first sampling point. Finally, the method comprises determining a second sampling point at which a next soil sample is to be (Continued)

collected and displaying the second sampling point in the field map.

16 Claims, 19 Drawing Sheets

(51) Int. Cl.
    *G01N 1/02*     (2006.01)
    *G06F 3/0482*     (2013.01)
    *G06Q 50/02*     (2012.01)

(52) U.S. Cl.
    CPC ....... *G06Q 50/02* (2013.01); *G01N 2001/021* (2013.01); *G01N 2033/245* (2013.01)

(58) Field of Classification Search
    CPC .. G01N 1/08; G01N 1/125; G01N 2001/1043; G01N 1/04; G01N 33/362; G01N 1/28; G01N 2001/021; G01N 2001/085; G01N 2001/4061; G01N 2033/245; G01N 33/24; E21B 49/025; E21B 49/02; E21B 25/00; E21B 7/046; E21B 19/08; E21B 7/021; E21B 7/02; E21B 7/26; B23Q 5/265; B23Q 5/326; B23Q 16/003; E01C 23/124; E04H 17/263; A01B 79/005; A01B 79/02; A01C 21/007; A01D 41/127
    USPC .................. 73/863, 864, 864.31, 864.32, 73/864.41–864.45; 173/19, 24, 25; 175/20
See application file for complete search history.

(56) References Cited

U.S. PATENT DOCUMENTS

| | | |
|---|---|---|
| 2003/0083819 A1 | 5/2003 | Rooney et al. |
| 2003/0182259 A1 | 9/2003 | Pickett et al. |
| 2012/0029933 A1* | 2/2012 | Zubiller ............... G06Q 10/101 |
| | | 705/2 |
| 2012/0101784 A1 | 4/2012 | Lindores et al. |
| 2015/0037805 A1 | 2/2015 | Zhang et al. |
| 2017/0042081 A1* | 2/2017 | Zumbach ................ G01N 1/08 |
| 2018/0005095 A1* | 1/2018 | Schindler, III ....... G06Q 10/087 |
| 2018/0130357 A1* | 5/2018 | Theriault .............. G08G 5/003 |
| 2018/0292339 A1 | 10/2018 | Gunzenhauser |

FOREIGN PATENT DOCUMENTS

| | | | |
|---|---|---|---|
| CN | 103930919 | | 7/2014 |
| CN | 104240134 A | * | 12/2014 |
| CN | 104574196 | | 4/2015 |
| CN | 104769631 | | 7/2015 |
| CN | 107077650 | | 8/2017 |

OTHER PUBLICATIONS

Current Claims in application No. PCT/US19/59206, dated Jan. 2020, 5 pages.

* cited by examiner

Fig. 2
(a)
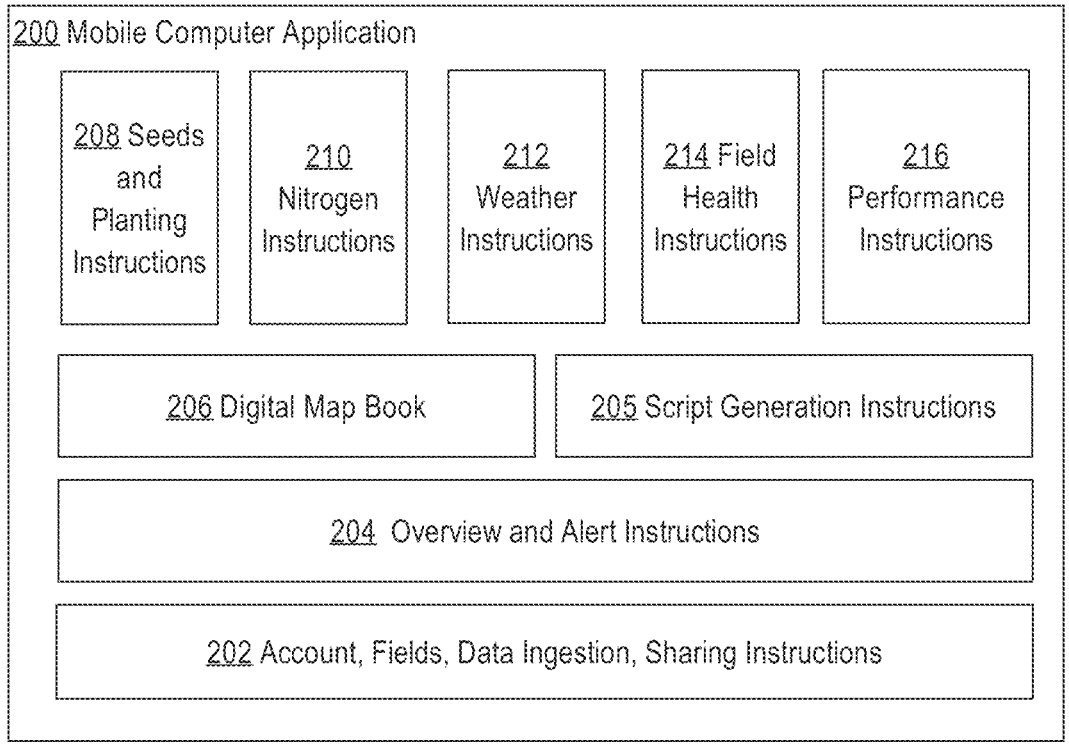
(b)
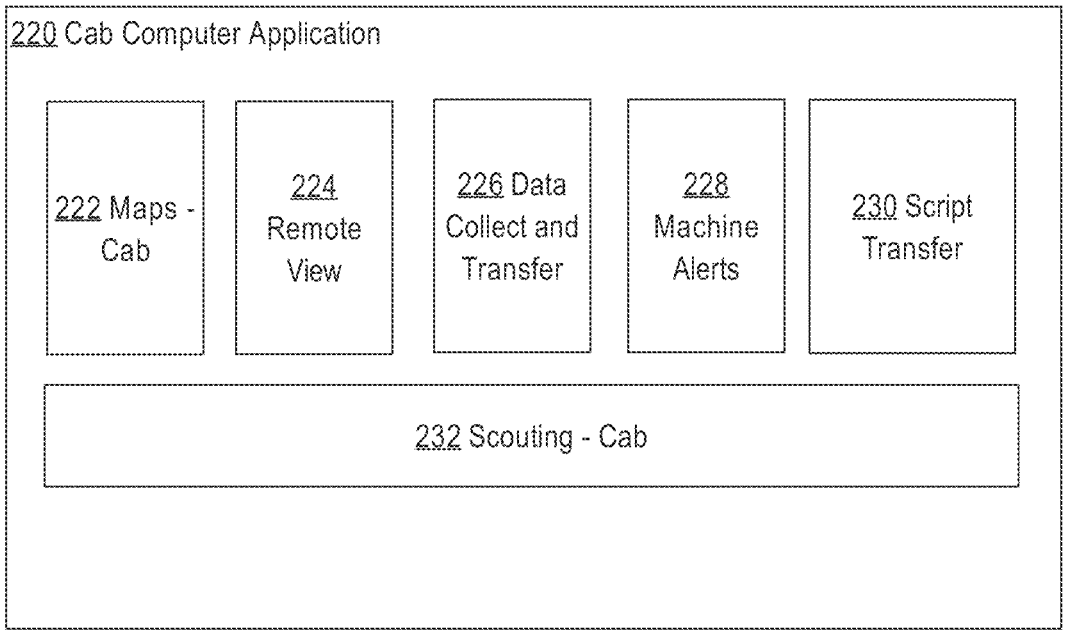

FIG. 5

Data Manager

| Nitrogen | Planting | Practices | Soil |

Planting 1(4 Fields)
Crop Corn Product
Plant Date: 2016-04-12
ILU 112 | Pop: 34000
[Edit] [Apply]

Planting 2(0 Fields)
Crop Corn Product
Plant Date: 2016-04-15
ILU 83 | Pop: 34000
[Edit] [Apply]

Planting 3(0 Fields)
Crop Corn Product
Plant Date: 2016-04-13
ILU 83 | Pop: 34000
[Edit] [Apply]

Planting 4(1 Fields)
Crop Corn Product
Plant Date: 2016-04-13
ILU 112 | Pop: 34000
[Edit] [Apply]

Add New Planting Plan [+]

| | CROP | PLANTED ACRES | PRODUCT | RELATIVE MATURITY | TARGET YIELD | POPULATION(AVG) | PLA |
|---|---|---|---|---|---|---|---|
| ☐ Select All | | | | | | | |
| ☐ Ames, IA 1<br>Corn \| 100 \| Boone, IA | Corn | --- | DMC82-M | 112 | 160 | 34000 | Apr |
| ☐ Austin, MN 1<br>Corn \| 100 \| Fredricks, MN | Corn | --- | DMC82-M | 114 | 160 | 36000 | Apr |
| ☐ Boone, IN 1<br>Corn \| 100 \| Boone, IA | Corn | --- | DMC82-M | 112 | 150 | 34000 | Apr |
| ☐ Champaign 1<br>Corn \| 100 \| Champaign, IL | Corn | --- | --- | 112 | 200 | 34000 | Apr |
| ☐ E Nebraska 1<br>Corn \| 100 \| Burt, NE | Corn | --- | --- | 112 | 160 | 34000 | Apr |

AUTOMATED SAMPLE COLLECTION AND TRACKING SYSTEM

BENEFIT CLAIM

This application claims the benefit under 35 U.S.C. § 119(e) of provisional application 62/753,692, filed Oct. 31, 2018, the entire contents of which is hereby incorporated by reference for all purposes as if fully set forth herein.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright or rights whatsoever. © 2015-2019 The Climate Corporation.

FIELD OF THE DISCLOSURE

The present disclosure relates to the technical field of agricultural sampling. The disclosure relates more specifically to the technical field of computer-implemented soil sample collection operation to automate the sample testing and ordering process. Another technical field is quality control and quality assurance of the soil sample data by streamlining the collection process.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

Soil sampling can help improve the health of a crop field and optimize crop production by providing physical characteristics such as pH level, acidity, macronutrients, or micronutrients. Soil sampling and testing are often carried out by manually identifying a sampling grid, manually tracking collection of the soil core, manually completing a laboratory order and sending the soil samples to a testing facility. Accordingly, existing approaches fail to enhance sample consistency and accurate record-keeping of the soil data. Thus, streamlined and automated methods and systems for collecting and tracking the soil samples may be desired.

SUMMARY

The appended claims may serve as a summary of the disclosure.

BRIEF DESCRIPTION OF THE DRAWINGS

In the drawings:

FIG. 2 illustrates two views of an example logical organization of sets of instructions in main memory when an example mobile application is loaded for execution.

FIG. 5 depicts an example embodiment of a timeline view for data entry.

FIG. 6 depicts an example embodiment of a spreadsheet view for data entry.

FIG. 10A, FIG. 10B, FIG. 10C, and FIG. 10D are screen snapshots of example computer-generated graphical user interfaces for tissue sampling and phenology sampling.

DETAILED DESCRIPTION

Figure 1:
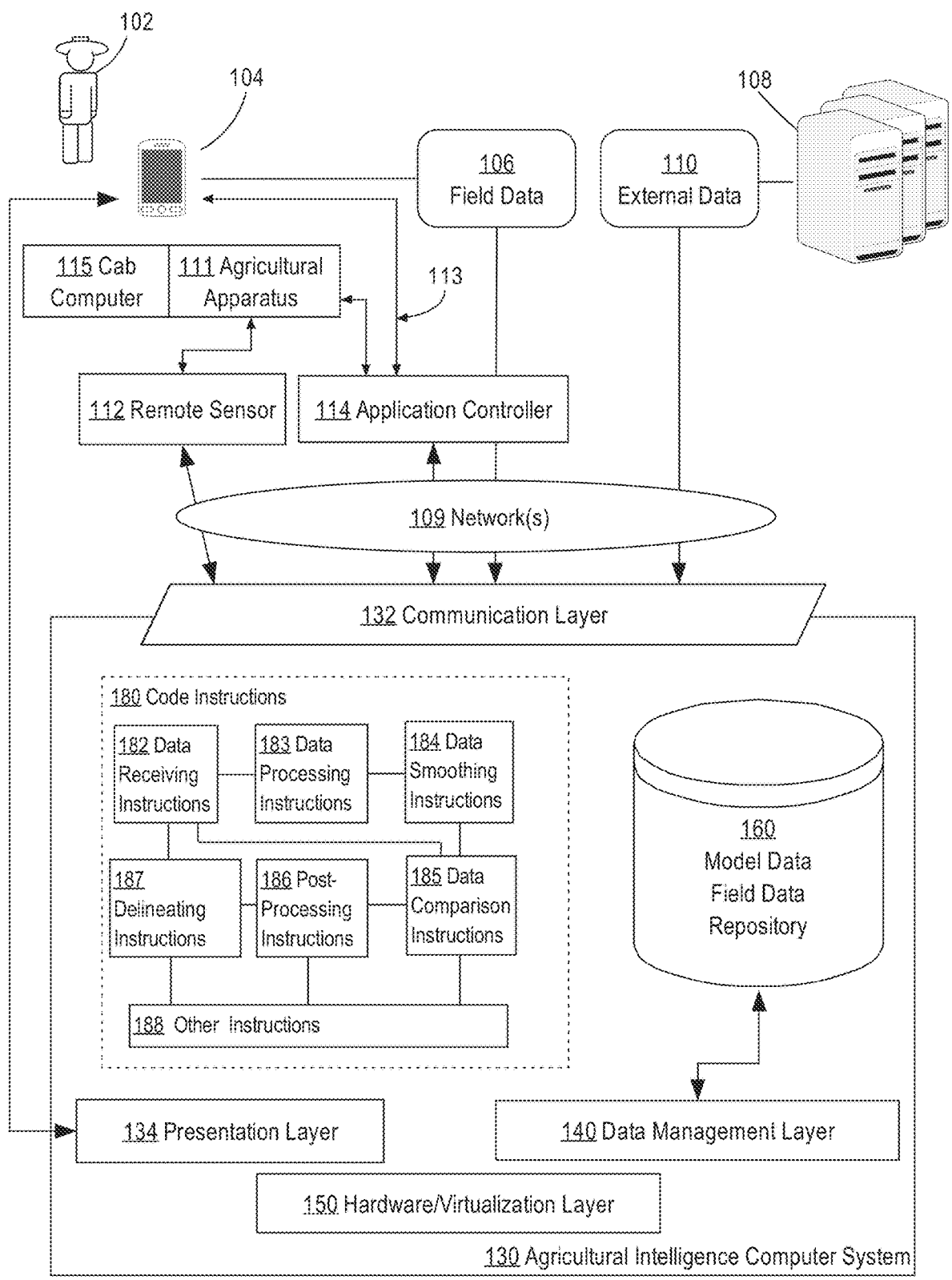
FIG. 1 illustrates an example computer system that is configured to perform the functions described herein, shown in a field environment with other apparatus with which the system may interoperate.

In the following description, for the purposes of explanation, numerous specific details are set forth in order to provide a thorough understanding of the present disclosure. It will be apparent, however, that embodiments may be practiced without these specific details. In other instances, well-known structures and devices are shown in block diagram form in order to avoid unnecessarily obscuring the present disclosure. Embodiments are disclosed in sections according to the following outline:

1. GENERAL OVERVIEW
2. EXAMPLE AGRICULTURAL INTELLIGENCE COMPUTER SYSTEM
   2.1. STRUCTURAL OVERVIEW
   2.2. APPLICATION PROGRAM OVERVIEW
   2.3. DATA INGEST TO THE COMPUTER SYSTEM
   2.4. PROCESS OVERVIEW—AGRONOMIC MODEL TRAINING
   2.5. IMPLEMENTATION EXAMPLE—HARDWARE OVERVIEW
3 FUNCTIONAL DESCRIPTION
   3.1 EXAMPLE PROCESSES
4 EXAMPLE COMPUTER-GENERATED GRAPHICAL USER INTERFACES
   4.1 GENERATING AN ORDER FOR SOIL SAMPLE AND IDENTIFYING THE FIELD
   4.2 SOIL SAMPLING
   4.3 TISSUE SAMPLING AND PHENOLOGY SAMPLING
   4.4 GENERATING A TAG BASED ON THE SAMPLING DATA
5 EXTENSIONS AND ALTERNATIVES
   5.1 NORMALIZING OR WEIGHTING AGRICULTURAL CHARACTERISTIC VALUES
   5.2 SELECTING SAMPLING LOCATIONS
   5.3 ALTERNATIVE PROCESS OF SELECTING A SAMPLING LOCATION
   5.4 MANAGEMENT ZONES IDENTIFYING MANAGEMENT ZONES BASED ON YIELD MAPS, SOIL MAPS, TOPOGRAPHY MAPS AND SATELLITE DATA
   5.5. PIPELINE FOR CREATING MANAGEMENT ZONES

1. General Overview

In various embodiments, a sampling system, process, or computer program product for automating soil sampling and tracking collection for accurate soil analysis is disclosed. The sample tracking system is configured to receive digitally stored field map data from a first data storage and digitally stored sampling data from a second data storage. The sample tracking system is programmed to display a field map comprising a first set of sampling points in a computer-generated graphical user interface. More specifically, each sampling point of the first set of sampling points is assigned to a corresponding section in the field map that is associated with a corresponding geographic coordinate Next, the sample tracking system is programmed to receive a selection of a first sampling point from among the first set of sampling points. Upon receiving the selection, the first sampling data for the first sampling point is displayed. The first sampling data includes a set of agricultural characteristics and a set of order data. When the collector completes soil sampling, an update indicating that a soil sample has been collected at the first sampling point can be received.

In some embodiments, the sample tracking system is configured to determine a second sampling point at which a next soil sample is to be collected based on a sampling protocol for the field map. In another embodiment, the sample tracking system can determine the second sampling point based on the geographic coordinates of the first set of sampling points. The sample tracking system is further programmed to display the second sampling point using visually different attributes compared to the first sampling point in the field map.

The sample tracking system has many technical benefits. First, the sample tracking system offers a unified and structured process for field observations, ensuring quality assurance and quality control of the sample data. Second, the sample tracking system is highly-scalable as it streamlines the data back to a centralized database and standardizing categorical variables. Third, the sampling tracking system resolves data irregularities and automates note collection of field samples by providing uniform unit measurement and reliable and consistent templates.

2. Example Agricultural Intelligence Computer System 2.1 Structural Overview FIG. 1 illustrates an example computer system that is configured to perform the functions described herein, shown in a field environment with other apparatus with which the system may interoperate. In one embodiment, a user 102 owns, operates or possesses a field manager computing device 104 in a field location or associated with a field location such as a field intended for agricultural activities or a management location for one or more agricultural fields. The field manager computer device 104 is programmed or configured to provide field data 106 to an agricultural intelligence computer system 130 via one or more networks 109.

Examples of field data 106 include (a) identification data (for example, acreage, field name, field identifiers, geographic identifiers, boundary identifiers, crop identifiers, and any other suitable data that may be used to identify farm land, such as a common land unit (CLU), lot and block number, a parcel number, geographic coordinates and boundaries, Farm Serial Number (FSN), farm number, tract number, field number, section, township, and/or range), (b) harvest data (for example, crop type, crop variety, crop rotation, whether the crop is grown organically, harvest date, Actual Production History (APH), expected yield, yield, crop price, crop revenue, grain moisture, tillage practice, and previous growing season information), (c) soil data (for example, type, composition, pH, organic matter (OM), cation exchange capacity (CEC)), (d) planting data (for example, planting date, seed(s) type, relative maturity (RM) of planted seed(s), seed population), (e) fertilizer data (for example, nutrient type (Nitrogen, Phosphorous, Potassium), application type, application date, amount, source, method), (f) chemical application data (for example, pesticide, herbicide, fungicide, other substance or mixture of substances intended for use as a plant regulator, defoliant, or desiccant, application date, amount, source, method), (g) irrigation data (for example, application date, amount, source, method), (h) weather data (for example, precipitation, rainfall rate, predicted rainfall, water runoff rate region, temperature, wind, forecast, pressure, visibility, clouds, heat index, dew point, humidity, snow depth, air quality, sunrise, sunset), (i) imagery data (for example, imagery and light spectrum information from an agricultural apparatus sensor, camera, computer, smartphone, tablet, unmanned aerial vehicle, planes or satellite), (j) scouting observations (photos, videos, free form notes, voice recordings, voice transcriptions, weather conditions (temperature, precipitation (current and over time), soil moisture, crop growth stage, wind velocity, relative humidity, dew point, black layer)), and (k) soil, seed, crop phenology, pest and disease reporting, and predictions sources and databases.

A data server computer 108 is communicatively coupled to agricultural intelligence computer system 130 and is programmed or configured to send external data 110 to agricultural intelligence computer system 130 via the network(s) 109. The external data server computer 108 may be owned or operated by the same legal person or entity as the agricultural intelligence computer system 130, or by a different person or entity such as a government agency, non-governmental organization (NGO), and/or a private data service provider. Examples of external data include weather data, imagery data, soil data, or statistical data relating to crop yields, among others. External data 110 may consist of the same type of information as field data 106. In some embodiments, the external data 110 is provided by an external data server 108 owned by the same entity that owns and/or operates the agricultural intelligence computer system 130. For example, the agricultural intelligence computer system 130 may include a data server focused exclusively on a type of data that might otherwise be obtained from third party sources, such as weather data. In some embodiments, an external data server 108 may actually be incorporated within the system 130.

An agricultural apparatus 111 may have one or more remote sensors 112 fixed thereon, which sensors are communicatively coupled either directly or indirectly via agricultural apparatus 111 to the agricultural intelligence computer system 130 and are programmed or configured to send sensor data to agricultural intelligence computer system 130. Examples of agricultural apparatus 111 include tractors, combines, harvesters, planters, trucks, fertilizer equipment, aerial vehicles including unmanned aerial vehicles, and any other item of physical machinery or hardware, typically mobile machinery, and which may be used in tasks associated with agriculture. In some embodiments, a single unit of apparatus 111 may comprise a plurality of sensors 112 that are coupled locally in a network on the apparatus; controller area network (CAN) is example of such a network that can be installed in combines, harvesters, sprayers, and cultivators. Application controller 114 is communicatively coupled to agricultural intelligence computer system 130 via the network(s) 109 and is programmed or configured to receive one or more scripts that are used to control an operating parameter of an agricultural vehicle or implement from the agricultural intelligence computer system 130. For instance, a controller area network (CAN) bus interface may be used to enable communications from the agricultural intelligence computer system 130 to the agricultural apparatus 111, such as how the CLIMATE FIELDVIEW DRIVE, available from The Climate Corporation, San Francisco, Calif., is used. Sensor data may consist of the same type of information as field data 106. In some embodiments, remote sensors 112 may not be fixed to an agricultural apparatus 111 but may be remotely located in the field and may communicate with network 109.

The apparatus 111 may comprise a cab computer 115 that is programmed with a cab application, which may comprise a version or variant of the mobile application for device 104 that is further described in other sections herein. In an embodiment, cab computer 115 comprises a compact computer, often a tablet-sized computer or smartphone, with a graphical screen display, such as a color display, that is mounted within an operator's cab of the apparatus 111. Cab computer 115 may implement some or all of the operations and functions that are described further herein for the mobile computer device 104.

The network(s) 109 broadly represent any combination of one or more data communication networks including local area networks, wide area networks, internetworks or internets, using any of wireline or wireless links, including terrestrial or satellite links. The network(s) may be implemented by any medium or mechanism that provides for the exchange of data between the various elements of FIG. 1. The various elements of FIG. 1 may also have direct (wired or wireless) communications links. The sensors 112, controller 114, external data server computer 108, and other elements of the system each comprise an interface compatible with the network(s) 109 and are programmed or configured to use standardized protocols for communication across the networks such as TCP/IP, Bluetooth, CAN protocol and higher-layer protocols such as HTTP, TLS, and the like.

Agricultural intelligence computer system 130 is programmed or configured to receive field data 106 from field manager computing device 104, external data 110 from external data server computer 108, and sensor data from remote sensor 112. Agricultural intelligence computer system 130 may be further configured to host, use or execute one or more computer programs, other software elements, digitally programmed logic such as FPGAs or ASICs, or any combination thereof to perform translation and storage of data values, construction of digital models of one or more crops on one or more fields, generation of recommendations and notifications, and generation and sending of scripts to application controller 114, in the manner described further in other sections of this disclosure.

In an embodiment, agricultural intelligence computer system 130 is programmed with or comprises a communication layer 132, presentation layer 134, data management layer 140, hardware/virtualization layer 150, and model and field data repository 160. "Layer," in this context, refers to any combination of electronic digital interface circuits, microcontrollers, firmware such as drivers, and/or computer programs or other software elements.

Communication layer 132 may be programmed or configured to perform input/output interfacing functions including sending requests to field manager computing device 104, external data server computer 108, and remote sensor 112 for field data, external data, and sensor data respectively. Communication layer 132 may be programmed or configured to send the received data to model and field data repository 160 to be stored as field data 106.

In an embodiment, agricultural intelligence computer system 130 is programmed with or comprises code instructions 180. For example, code instructions 180 may include data receiving instructions 182 which are programmed for receiving, over network(s) 109, electronic digital data comprising field data, sampling data, and yield data. Code instructions 180 may also include data processing instructions 183 which are programmed for preprocessing of the received field data, sampling data, and yield data; data smoothing instructions 184 which are programmed for smoothing the preprocessed field data, sampling data, and yield data; data delineating instructions 187 which are programmed for delineating management zones (e.g., sections) and sampling points; post-processing instructions 186 which are programmed for post-processing of the delineated management zones and sampling points; data comparison instructions 185 which are programmed for comparing the sampling points and post-processed management zones; and other detection instructions 188.

Presentation layer 134 may be programmed or configured to generate a graphical user interface (GUI) to be displayed on field manager computing device 104, cab computer 115 or other computers that are coupled to the system 130 through the network 109. The GUI may comprise controls for inputting data to be sent to agricultural intelligence computer system 130, generating requests for models and/or recommendations, and/or displaying recommendations, notifications, models, and other field data.

Data management layer 140 may be programmed or configured to manage read operations and write operations involving the repository 160 and other functional elements of the system, including queries and result sets communicated between the functional elements of the system and the repository. Examples of data management layer 140 include JDBC, SQL server interface code, and/or HADOOP interface code, among others. Repository 160 may comprise a database. As used herein, the term "database" may refer to either a body of data, a relational database management system (RDBMS), or to both. As used herein, a database may comprise any collection of data including hierarchical databases, relational databases, flat file databases, object-relational databases, object oriented databases, distributed databases, and any other structured collection of records or data that is stored in a computer system. Examples of RDBMS's include, but are not limited to including, ORACLE®, MYSQL, IBM® DB2, MICROSOFT® SQL SERVER, SYBASE®, and POSTGRESQL databases. However, any database may be used that enables the systems and methods described herein.

When field data 106 is not provided directly to the agricultural intelligence computer system via one or more agricultural machines or agricultural machine devices that interacts with the agricultural intelligence computer system, the user may be prompted via one or more user interfaces on the user device (served by the agricultural intelligence computer system) to input such information. In an example embodiment, the user may specify identification data by accessing a map on the user device (served by the agricultural intelligence computer system) and selecting specific CLUs that have been graphically shown on the map. In an alternative embodiment, the user 102 may specify identification data by accessing a map on the user device (served by the agricultural intelligence computer system 130) and drawing boundaries of the field over the map. Such CLU selection or map drawings represent geographic identifiers. In alternative embodiments, the user may specify identification data by accessing field identification data (provided as shape files or in a similar format) from the U. S. Department of Agriculture Farm Service Agency or other source via the user device and providing such field identification data to the agricultural intelligence computer system.

In an example embodiment, the agricultural intelligence computer system 130 is programmed to generate and cause displaying a graphical user interface comprising a data manager for data input. After one or more fields have been identified using the methods described above, the data manager may provide one or more graphical user interface widgets which when selected can identify changes to the field, soil, crops, tillage, or nutrient practices. The data manager may include a timeline view, a spreadsheet view, and/or one or more editable programs.

Figure 5:
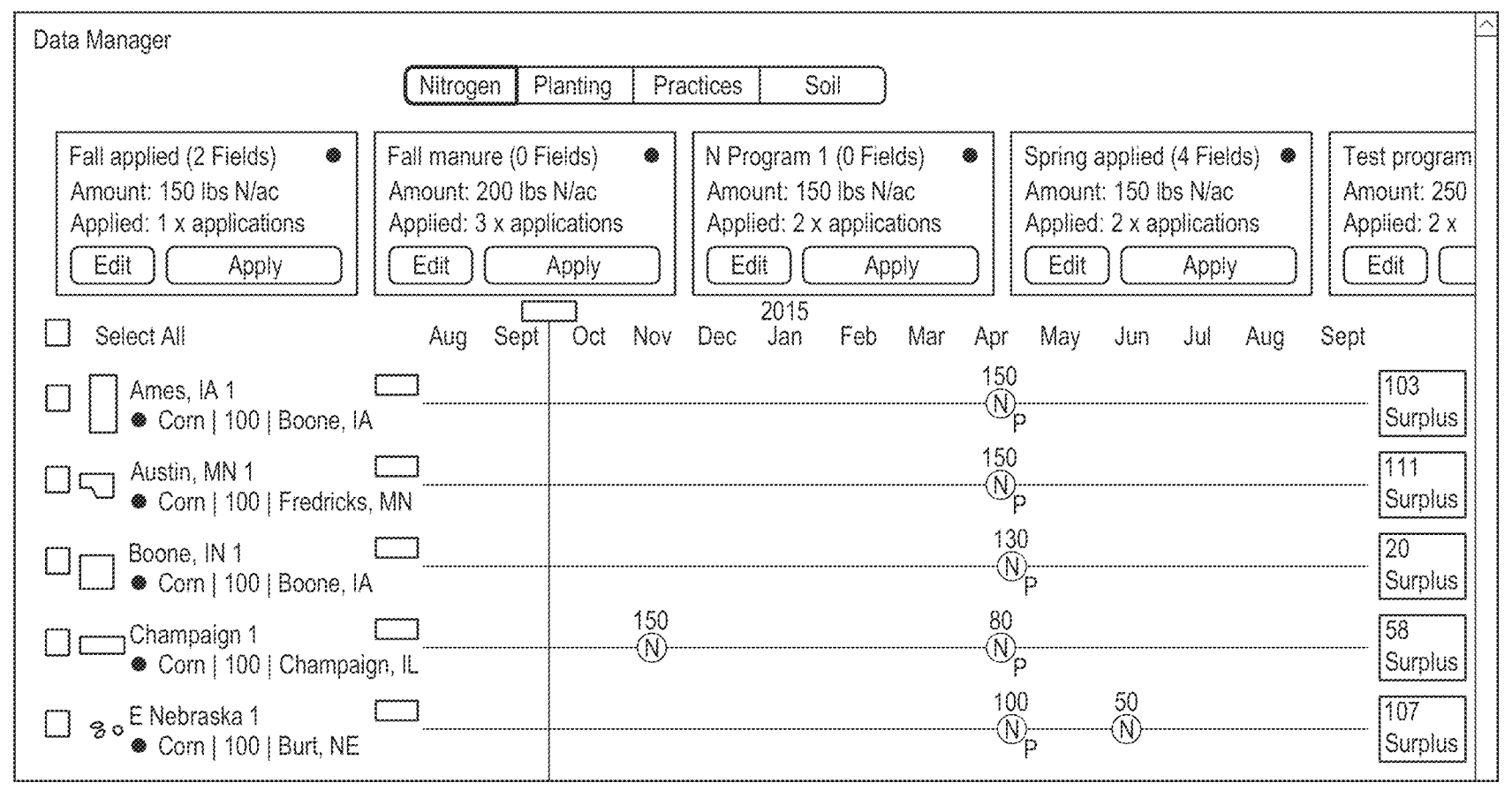

FIG. 5 depicts an example embodiment of a timeline view for data entry. Using the display depicted in FIG. 5, a user computer can input a selection of a particular field and a particular date for the addition of event. Events depicted at the top of the timeline may include Nitrogen, Planting, Practices, and Soil. To add a nitrogen application event, a user computer may provide input to select the nitrogen tab. The user computer may then select a location on the timeline for a particular field in order to indicate an application of nitrogen on the selected field. In response to receiving a selection of a location on the timeline for a particular field, the data manager may display a data entry overlay, allowing the user computer to input data pertaining to nitrogen applications, planting procedures, soil application, tillage procedures, irrigation practices, or other information relating to the particular field. For example, if a user computer selects a portion of the timeline and indicates an application of nitrogen, then the data entry overlay may include fields for inputting an amount of nitrogen applied, a date of application, a type of fertilizer used, and any other information related to the application of nitrogen.

In an embodiment, the data manager provides an interface for creating one or more programs. "Program," in this context, refers to a set of data pertaining to nitrogen applications, planting procedures, soil application, tillage procedures, irrigation practices, or other information that may be related to one or more fields, and that can be stored in digital data storage for reuse as a set in other operations. After a program has been created, it may be conceptually applied to one or more fields and references to the program may be stored in digital storage in association with data identifying the fields. Thus, instead of manually entering identical data relating to the same nitrogen applications for multiple different fields, a user computer may create a program that indicates a particular application of nitrogen and then apply the program to multiple different fields. For example, in the timeline view of FIG. 5, the top two timelines have the "Spring applied" program selected, which includes an application of 150 lbs N/ac in early April. The data manager may provide an interface for editing a program. In an embodiment, when a particular program is edited, each field that has selected the particular program is edited. For example, in FIG. 5, if the "Spring applied" program is edited to reduce the application of nitrogen to 130 lbs N/ac, the top two fields may be updated with a reduced application of nitrogen based on the edited program.

In an embodiment, in response to receiving edits to a field that has a program selected, the data manager removes the correspondence of the field to the selected program. For example, if a nitrogen application is added to the top field in FIG. 5, the interface may update to indicate that the "Spring applied" program is no longer being applied to the top field. While the nitrogen application in early April may remain, updates to the "Spring applied" program would not alter the April application of nitrogen.

FIG. 6 depicts an example embodiment of a spreadsheet view for data entry. Using the display depicted in FIG. 6, a user can create and edit information for one or more fields. The data manager may include spreadsheets for inputting information with respect to Nitrogen, Planting, Practices, and Soil as depicted in FIG. 6. To edit a particular entry, a user computer may select the particular entry in the spreadsheet and update the values. For example, FIG. 6 depicts an in-progress update to a target yield value for the second field. Additionally, a user computer may select one or more fields in order to apply one or more programs. In response to receiving a selection of a program for a particular field, the data manager may automatically complete the entries for the particular field based on the selected program. As with the timeline view, the data manager may update the entries for each field associated with a particular program in response to receiving an update to the program. Additionally, the data manager may remove the correspondence of the selected program to the field in response to receiving an edit to one of the entries for the field.

In an embodiment, model and field data is stored in model and field data repository 160. Model data comprises data models created for one or more fields. For example, a crop model may include a digitally constructed model of the development of a crop on the one or more fields. "Model," in this context, refers to an electronic digitally stored set of executable instructions and data values, associated with one another, which are capable of receiving and responding to a programmatic or other digital call, invocation, or request for resolution based upon specified input values, to yield one or more stored or calculated output values that can serve as the basis of computer-implemented recommendations, output data displays, or machine control, among other things. Persons of skill in the field find it convenient to express models using mathematical equations, but that form of expression does not confine the models disclosed herein to abstract concepts; instead, each model herein has a practical application in a computer in the form of stored executable instructions and data that implement the model using the computer. The model may include a model of past events on the one or more fields, a model of the current status of the one or more fields, and/or a model of predicted events on the one or more fields. Model and field data may be stored in data structures in memory, rows in a database table, in flat files or spreadsheets, or other forms of stored digital data.

In an embodiment, agricultural intelligence computer system 130 is programmed with or comprises a sampling server ("server") 170. The server 170 is further configured to comprise a location selection module 174 and a client interface 176. The location selection module 174 is configured to select locations for validating modeling results. The locations selected can depend on modeling needs. The location selection module 174 can also be configured to evaluate the selected locations. The client interface 176 is configured to communicate with a client device, such as a field manager computing device 104 or a cab computer 115, over a communication network, through the communication layer 132. The communication can include receiving input data, such as field data, model data, or user objectives, and transmitting output data, such as information regarding selected locations. The client interface 176 can also be configured to communicate with a display device or a remote system that develops or maintains an agricultural modeling tool.

Each component of the server 170 comprises a set of one or more pages of main memory, such as RAM, in the agricultural intelligence computer system 130 into which executable instructions have been loaded and which when executed cause the agricultural intelligence computing system to perform the functions or operations that are described herein with reference to those modules. For example, the location selection module 174 may comprise a set of pages in RAM that contain instructions which when executed cause performing the location selection functions that are described herein. The instructions may be in machine executable code in the instruction set of a CPU and may have been compiled based upon source code written in JAVA, C, C++, OBJECTIVE-C, or any other human-readable programming language or environment, alone or in combination with scripts in JAVASCRIPT, other scripting languages and other programming source text. The term "pages" is intended to refer broadly to any region within main memory and the specific terminology used in a system may vary depending on the memory architecture or processor architecture. In another embodiment, each component of the server 170 also may represent one or more files or projects of source code that are digitally stored in a mass storage device such as non-volatile RAM or disk storage, in the agricultural intelligence computer system 130 or a separate repository system, which when compiled or interpreted cause generating executable instructions which when executed cause the agricultural intelligence computing system to perform the functions or operations that are described herein with reference to those modules. In other words, the drawing figure may represent the manner in which programmers or software developers organize and arrange source code for later compilation into an executable, or interpretation into bytecode or the equivalent, for execution by the agricultural intelligence computer system 130.

Figure 4:
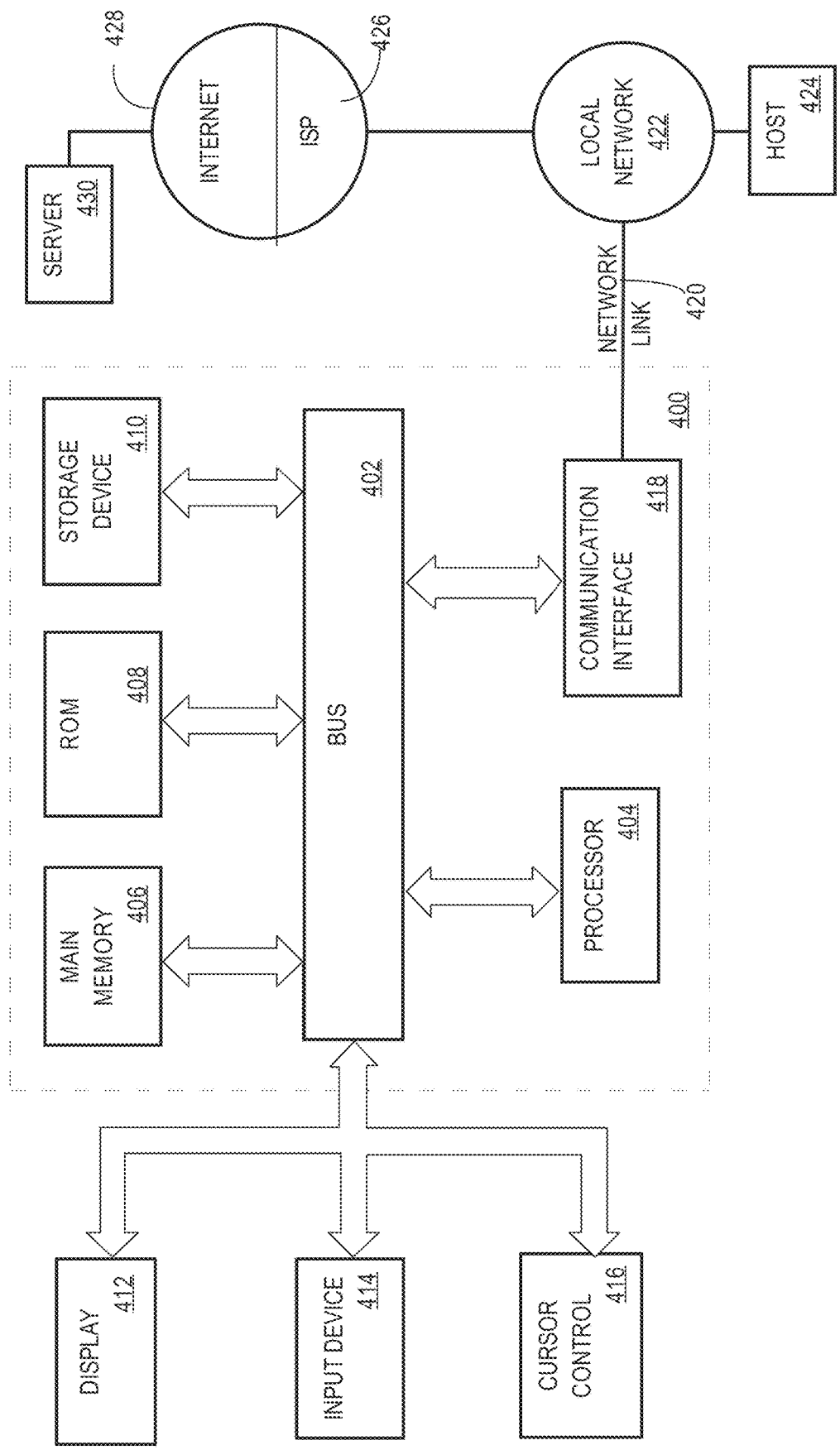
FIG. 4 is a block diagram that illustrates a computer system upon which an embodiment of the invention may be implemented.

Hardware/virtualization layer 150 comprises one or more central processing units (CPUs), memory controllers, and other devices, components, or elements of a computer system such as volatile or non-volatile memory, non-volatile storage such as disk, and I/O devices or interfaces as illustrated and described, for example, in connection with FIG. 4. The layer 150 also may comprise programmed instructions that are configured to support virtualization, containerization, or other technologies.

For purposes of illustrating a clear example, FIG. 1 shows a limited number of instances of certain functional elements. However, in other embodiments, there may be any number of such elements. For example, embodiments may use thousands or millions of different mobile computing devices 104 associated with different users. Further, the system 130 and/or external data server computer 108 may be implemented using two or more processors, cores, clusters, or instances of physical machines or virtual machines, configured in a discrete location or co-located with other elements in a datacenter, shared computing facility or cloud computing facility.

2.2. Application Program Overview

In an embodiment, the implementation of the functions described herein using one or more computer programs or other software elements that are loaded into and executed using one or more general-purpose computers will cause the general-purpose computers to be configured as a particular machine or as a computer that is specially adapted to perform the functions described herein. Further, each of the flow diagrams that are described further herein may serve, alone or in combination with the descriptions of processes and functions in prose herein, as algorithms, plans or directions that may be used to program a computer or logic to implement the functions that are described. In other words, all the prose text herein, and all the drawing figures, together are intended to provide disclosure of algorithms, plans or directions that are sufficient to permit a skilled person to program a computer to perform the functions that are described herein, in combination with the skill and knowledge of such a person given the level of skill that is appropriate for inventions and disclosures of this type.

In an embodiment, user 102 interacts with agricultural intelligence computer system 130 using field manager computing device 104 configured with an operating system and one or more application programs or apps; the field manager computing device 104 also may interoperate with the agricultural intelligence computer system independently and automatically under program control or logical control and direct user interaction is not always required. Field manager computing device 104 broadly represents one or more of a smart phone, PDA, tablet computing device, laptop computer, desktop computer, workstation, or any other computing device capable of transmitting and receiving information and performing the functions described herein. Field manager computing device 104 may communicate via a network using a mobile application stored on field manager computing device 104, and in some embodiments, the device may be coupled using a cable 113 or connector to the sensor 112 and/or controller 114. A particular user 102 may own, operate or possess and use, in connection with system 130, more than one field manager computing device 104 at a time.

The mobile application may provide client-side functionality, via the network to one or more mobile computing devices. In an example embodiment, field manager computing device 104 may access the mobile application via a web browser or a local client application or app. Field manager computing device 104 may transmit data to, and receive data from, one or more front-end servers, using web-based protocols or formats such as HTTP, XML, and/or JSON, or app-specific protocols. In an example embodiment, the data may take the form of requests and user information input, such as field data, into the mobile computing device. In some embodiments, the mobile application interacts with location tracking hardware and software on field manager computing device 104 which determines the location of field manager computing device 104 using standard tracking techniques such as multilateration of radio signals, the global positioning system (GPS), WiFi positioning systems, or other methods of mobile positioning. In some cases, location data or other data associated with the device 104, user 102, and/or user account(s) may be obtained by queries to an operating system of the device or by requesting an app on the device to obtain data from the operating system.

In an embodiment, field manager computing device 104 sends field data 106 to agricultural intelligence computer system 130 comprising or including, but not limited to, data values representing one or more of: a geographical location of the one or more fields, tillage information for the one or more fields, crops planted in the one or more fields, and soil data extracted from the one or more fields. Field manager computing device 104 may send field data 106 in response to user input from user 102 specifying the data values for the one or more fields. Additionally, field manager computing device 104 may automatically send field data 106 when one or more of the data values becomes available to field manager computing device 104. For example, field manager computing device 104 may be communicatively coupled to remote sensor 112 and/or application controller 114 which include an irrigation sensor and/or irrigation controller. In response to receiving data indicating that application controller 114 released water onto the one or more fields, field manager computing device 104 may send field data 106 to agricultural intelligence computer system 130 indicating that water was released on the one or more fields. Field data 106 identified in this disclosure may be input and communicated using electronic digital data that is communicated between computing devices using parameterized URLs over HTTP, or another suitable communication or messaging protocol.

A commercial example of the mobile application is CLIMATE FIELDVIEW, commercially available from The Climate Corporation, San Francisco, Calif. The CLIMATE FIELDVIEW application, or other applications, may be modified, extended, or adapted to include features, functions, and programming that have not been disclosed earlier than the filing date of this disclosure. In one embodiment, the mobile application comprises an integrated software platform that allows a grower to make fact-based decisions for their operation because it combines historical data about the grower's fields with any other data that the grower wishes to compare. The combinations and comparisons may be performed in real time and are based upon scientific models that provide potential scenarios to permit the grower to make better, more informed decisions.

FIG. 2 illustrates two views of an example logical organization of sets of instructions in main memory when an example mobile application is loaded for execution. In FIG. 2, each named element represents a region of one or more pages of RAM or other main memory, or one or more blocks of disk storage or other non-volatile storage, and the programmed instructions within those regions. In one embodiment, in view (a), a mobile computer application 200 comprises account-fields-data ingestion-sharing instructions 202, overview and alert instructions 204, digital map book instructions 206, seeds and planting instructions 208, nitrogen instructions 210, weather instructions 212, field health instructions 214, and performance instructions 216.

In one embodiment, a mobile computer application 200 comprises account, fields, data ingestion, sharing instructions 202 which are programmed to receive, translate, and ingest field data from third party systems via manual upload or APIs. Data types may include field boundaries, yield maps, as-planted maps, soil test results, as-applied maps, and/or management zones, among others. Data formats may include shape files, native data formats of third parties, and/or farm management information system (FMIS) exports, among others. Receiving data may occur via manual upload, e-mail with attachment, external APIs that push data to the mobile application, or instructions that call APIs of external systems to pull data into the mobile application. In one embodiment, mobile computer application 200 comprises a data inbox. In response to receiving a selection of the data inbox, the mobile computer application 200 may display a graphical user interface for manually uploading data files and importing uploaded files to a data manager.

In one embodiment, digital map book instructions 206 comprise field map data layers stored in device memory and are programmed with data visualization tools and geospatial field notes. This provides growers with convenient information close at hand for reference, logging and visual insights into field performance. In one embodiment, overview and alert instructions 204 are programmed to provide an operation-wide view of what is important to the grower, and timely recommendations to take action or focus on particular issues. This permits the grower to focus time on what needs attention, to save time and preserve yield throughout the season. In one embodiment, seeds and planting instructions 208 are programmed to provide tools for seed selection, hybrid placement, and script creation, including variable rate (VR) script creation, based upon scientific models and empirical data. This enables growers to maximize yield or return on investment through optimized seed purchase, placement and population.

In one embodiment, script generation instructions 205 are programmed to provide an interface for generating scripts, including variable rate (VR) fertility scripts. The interface enables growers to create scripts for field implements, such as nutrient applications, planting, and irrigation. For example, a planting script interface may comprise tools for identifying a type of seed for planting. Upon receiving a selection of the seed type, mobile computer application 200 may display one or more fields broken into management zones, such as the field map data layers created as part of digital map book instructions 206. In one embodiment, the management zones comprise soil zones along with a panel identifying each soil zone and a soil name, texture, drainage for each zone, or other field data. Mobile computer application 200 may also display tools for editing or creating such, such as graphical tools for drawing management zones, such as soil zones, over a map of one or more fields. Planting procedures may be applied to all management zones or different planting procedures may be applied to different subsets of management zones. When a script is created, mobile computer application 200 may make the script available for download in a format readable by an application controller, such as an archived or compressed format. Additionally, and/or alternatively, a script may be sent directly to cab computer 115 from mobile computer application 200 and/or uploaded to one or more data servers and stored for further use.

In one embodiment, nitrogen instructions 210 are programmed to provide tools to inform nitrogen decisions by visualizing the availability of nitrogen to crops. This enables growers to maximize yield or return on investment through optimized nitrogen application during the season. Example programmed functions include displaying images such as SSURGO images to enable drawing of fertilizer application zones and/or images generated from subfield soil data, such as data obtained from sensors, at a high spatial resolution (as fine as millimeters or smaller depending on sensor proximity and resolution); upload of existing grower-defined zones; providing a graph of plant nutrient availability and/or a map to enable tuning application(s) of nitrogen across multiple zones; output of scripts to drive machinery; tools for mass data entry and adjustment; and/or maps for data visualization, among others. "Mass data entry," in this context, may mean entering data once and then applying the same data to multiple fields and/or zones that have been defined in the system; example data may include nitrogen application data that is the same for many fields and/or zones of the same grower, but such mass data entry applies to the entry of any type of field data into the mobile computer application 200. For example, nitrogen instructions 210 may be programmed to accept definitions of nitrogen application and practices programs and to accept user input specifying to apply those programs across multiple fields. "Nitrogen application programs," in this context, refers to stored, named sets of data that associates: a name, color code or other identifier, one or more dates of application, types of material or product for each of the dates and amounts, method of application or incorporation such as injected or broadcast, and/or amounts or rates of application for each of the dates, crop or hybrid that is the subject of the application, among others. "Nitrogen practices programs," in this context, refer to stored, named sets of data that associates: a practices name; a previous crop; a tillage system; a date of primarily tillage; one or more previous tillage systems that were used; one or more indicators of application type, such as manure, that were used. Nitrogen instructions 210 also may be programmed to generate and cause displaying a nitrogen graph, which indicates projections of plant use of the specified nitrogen and whether a surplus or shortfall is predicted; in some embodiments, different color indicators may signal a magnitude of surplus or magnitude of shortfall. In one embodiment, a nitrogen graph comprises a graphical display in a computer display device comprising a plurality of rows, each row associated with and identifying a field; data specifying what crop is planted in the field, the field size, the field location, and a graphic representation of the field perimeter; in each row, a timeline by month with graphic indicators specifying each nitrogen application and amount at points correlated to month names; and numeric and/or colored indicators of surplus or shortfall, in which color indicates magnitude.

In one embodiment, the nitrogen graph may include one or more user input features, such as dials or slider bars, to dynamically change the nitrogen planting and practices programs so that a user may optimize his nitrogen graph. The user may then use his optimized nitrogen graph and the related nitrogen planting and practices programs to implement one or more scripts, including variable rate (VR) fertility scripts. Nitrogen instructions 210 also may be programmed to generate and cause displaying a nitrogen map, which indicates projections of plant use of the specified nitrogen and whether a surplus or shortfall is predicted; in some embodiments, different color indicators may signal a magnitude of surplus or magnitude of shortfall. The nitrogen map may display projections of plant use of the specified nitrogen and whether a surplus or shortfall is predicted for different times in the past and the future (such as daily, weekly, monthly or yearly) using numeric and/or colored indicators of surplus or shortfall, in which color indicates magnitude. In one embodiment, the nitrogen map may include one or more user input features, such as dials or slider bars, to dynamically change the nitrogen planting and practices programs so that a user may optimize his nitrogen map, such as to obtain a preferred amount of surplus to shortfall. The user may then use his optimized nitrogen map and the related nitrogen planting and practices programs to implement one or more scripts, including variable rate (VR) fertility scripts. In other embodiments, similar instructions to the nitrogen instructions 210 could be used for application of other nutrients (such as phosphorus and potassium), application of pesticide, and irrigation programs.

In one embodiment, weather instructions 212 are programmed to provide field-specific recent weather data and forecasted weather information. This enables growers to save time and have an efficient integrated display with respect to daily operational decisions.

In one embodiment, field health instructions 214 are programmed to provide timely remote sensing images highlighting in-season crop variation and potential concerns. Example programmed functions include cloud checking, to identify possible clouds or cloud shadows; determining nitrogen indices based on field images; graphical visualization of scouting layers, including, for example, those related to field health, and viewing and/or sharing of scouting notes; and/or downloading satellite images from multiple sources and prioritizing the images for the grower, among others.

In one embodiment, performance instructions 216 are programmed to provide reports, analysis, and insight tools using on-farm data for evaluation, insights and decisions. This enables the grower to seek improved outcomes for the next year through fact-based conclusions about why return on investment was at prior levels, and insight into yield-limiting factors. The performance instructions 216 may be programmed to communicate via the network(s) 109 to back-end analytics programs executed at agricultural intelligence computer system 130 and/or external data server computer 108 and configured to analyze metrics such as yield, yield differential, hybrid, population, SSURGO zone, soil test properties, or elevation, among others. Programmed reports and analysis may include yield variability analysis, treatment effect estimation, benchmarking of yield and other metrics against other growers based on anonymized data collected from many growers, or data for seeds and planting, among others.

Applications having instructions configured in this way may be implemented for different computing device platforms while retaining the same general user interface appearance. For example, the mobile application may be programmed for execution on tablets, smartphones, or server computers that are accessed using browsers at client computers. Further, the mobile application as configured for tablet computers or smartphones may provide a full app experience or a cab app experience that is suitable for the display and processing capabilities of cab computer 115. For example, referring now to view (b) of FIG. 2, in one embodiment a cab computer application 220 may comprise maps-cab instructions 222, remote view instructions 224, data collect and transfer instructions 226, machine alerts instructions 228, script transfer instructions 230, and scouting-cab instructions 232. The code base for the instructions of view (b) may be the same as for view (a) and executables implementing the code may be programmed to detect the type of platform on which they are executing and to expose, through a graphical user interface, only those functions that are appropriate to a cab platform or full platform. This approach enables the system to recognize the distinctly different user experience that is appropriate for an in-cab environment and the different technology environment of the cab. The maps-cab instructions 222 may be programmed to provide map views of fields, farms or regions that are useful in directing machine operation. The remote view instructions 224 may be programmed to turn on, manage, and provide views of machine activity in real-time or near real-time to other computing devices connected to the system 130 via wireless networks, wired connectors or adapters, and the like. The data collect and transfer instructions 226 may be programmed to turn on, manage, and provide transfer of data collected at sensors and controllers to the system 130 via wireless networks, wired connectors or adapters, and the like. The machine alerts instructions 228 may be programmed to detect issues with operations of the machine or tools that are associated with the cab and generate operator alerts. The script transfer instructions 230 may be configured to transfer in scripts of instructions that are configured to direct machine operations or the collection of data. The scouting-cab instructions 232 may be programmed to display location-based alerts and information received from the system 130 based on the location of the field manager computing device 104, agricultural apparatus 111, or sensors 112 in the field and ingest, manage, and provide transfer of location-based scouting observations to the system 130 based on the location of the agricultural apparatus 111 or sensors 112 in the field.

2.3. Data Ingest to the Computer System

In an embodiment, external data server computer 108 stores external data 110, including soil data representing soil composition for the one or more fields and weather data representing temperature and precipitation on the one or more fields. The weather data may include past and present weather data as well as forecasts for future weather data. In an embodiment, external data server computer 108 comprises a plurality of servers hosted by different entities. For example, a first server may contain soil composition data while a second server may include weather data. Additionally, soil composition data may be stored in multiple servers. For example, one server may store data representing percentage of sand, silt, and clay in the soil while a second server may store data representing percentage of organic matter (OM) in the soil.

In an embodiment, remote sensor 112 comprises one or more sensors that are programmed or configured to produce one or more observations. Remote sensor 112 may be aerial sensors, such as satellites, vehicle sensors, planting equipment sensors, tillage sensors, fertilizer or insecticide application sensors, harvester sensors, and any other implement capable of receiving data from the one or more fields. In an embodiment, application controller 114 is programmed or configured to receive instructions from agricultural intelligence computer system 130. Application controller 114 may also be programmed or configured to control an operating parameter of an agricultural vehicle or implement. For example, an application controller may be programmed or configured to control an operating parameter of a vehicle, such as a tractor, planting equipment, tillage equipment, fertilizer or insecticide equipment, harvester equipment, or other farm implements such as a water valve. Other embodiments may use any combination of sensors and controllers, of which the following are merely selected examples.

The system 130 may obtain or ingest data under user 102 control, on a mass basis from a large number of growers who have contributed data to a shared database system. This form of obtaining data may be termed "manual data ingest" as one or more user-controlled computer operations are requested or triggered to obtain data for use by the system 130. As an example, the CLIMATE FIELDVIEW application, commercially available from The Climate Corporation, San Francisco, Calif., may be operated to export data to system 130 for storing in the repository 160.

For example, seed monitor systems can both control planter apparatus components and obtain planting data, including signals from seed sensors via a signal harness that comprises a CAN backbone and point-to-point connections for registration and/or diagnostics. Seed monitor systems can be programmed or configured to display seed spacing, population and other information to the user via the cab computer 115 or other devices within the system 130. Examples are disclosed in U.S. Pat. No. 8,738,243 and US Pat. Pub. 20150094916, and the present disclosure assumes knowledge of those other patent disclosures.

Likewise, yield monitor systems may contain yield sensors for harvester apparatus that send yield measurement data to the cab computer 115 or other devices within the system 130. Yield monitor systems may utilize one or more remote sensors 112 to obtain grain moisture measurements in a combine or other harvester and transmit these measurements to the user via the cab computer 115 or other devices within the system 130.

In an embodiment, examples of sensors 112 that may be used with any moving vehicle or apparatus of the type described elsewhere herein include kinematic sensors and position sensors. Kinematic sensors may comprise any of speed sensors such as radar or wheel speed sensors, accelerometers, or gyros. Position sensors may comprise GPS receivers or transceivers, or WiFi-based position or mapping apps that are programmed to determine location based upon nearby WiFi hotspots, among others.

In an embodiment, examples of sensors 112 that may be used with tractors or other moving vehicles include engine speed sensors, fuel consumption sensors, area counters or distance counters that interact with GPS or radar signals, PTO (power take-off) speed sensors, tractor hydraulics sensors configured to detect hydraulics parameters such as pressure or flow, and/or and hydraulic pump speed, wheel speed sensors or wheel slippage sensors. In an embodiment, examples of controllers 114 that may be used with tractors include hydraulic directional controllers, pressure controllers, and/or flow controllers; hydraulic pump speed controllers; speed controllers or governors; hitch position controllers; or wheel position controllers provide automatic steering.

In an embodiment, examples of sensors 112 that may be used with seed planting equipment such as planters, drills, or air seeders include seed sensors, which may be optical, electromagnetic, or impact sensors; downforce sensors such as load pins, load cells, pressure sensors; soil property sensors such as reflectivity sensors, moisture sensors, electrical conductivity sensors, optical residue sensors, or temperature sensors; component operating criteria sensors such as planting depth sensors, downforce cylinder pressure sensors, seed disc speed sensors, seed drive motor encoders, seed conveyor system speed sensors, or vacuum level sensors; or pesticide application sensors such as optical or other electromagnetic sensors, or impact sensors. In an embodiment, examples of controllers 114 that may be used with such seed planting equipment include: toolbar fold controllers, such as controllers for valves associated with hydraulic cylinders; downforce controllers, such as controllers for valves associated with pneumatic cylinders, airbags, or hydraulic cylinders, and programmed for applying downforce to individual row units or an entire planter frame; planting depth controllers, such as linear actuators; metering controllers, such as electric seed meter drive motors, hydraulic seed meter drive motors, or swath control clutches; hybrid selection controllers, such as seed meter drive motors, or other actuators programmed for selectively allowing or preventing seed or an air-seed mixture from delivering seed to or from seed meters or central bulk hoppers; metering controllers, such as electric seed meter drive motors, or hydraulic seed meter drive motors; seed conveyor system controllers, such as controllers for a belt seed delivery conveyor motor; marker controllers, such as a controller for a pneumatic or hydraulic actuator; or pesticide application rate controllers, such as metering drive controllers, orifice size or position controllers.

In an embodiment, examples of sensors 112 that may be used with tillage equipment include position sensors for tools such as shanks or discs; tool position sensors for such tools that are configured to detect depth, gang angle, or lateral spacing; downforce sensors; or draft force sensors. In an embodiment, examples of controllers 114 that may be used with tillage equipment include downforce controllers or tool position controllers, such as controllers configured to control tool depth, gang angle, or lateral spacing.

In an embodiment, examples of sensors 112 that may be used in relation to apparatus for applying fertilizer, insecticide, fungicide and the like, such as on-planter starter fertilizer systems, subsoil fertilizer applicators, or fertilizer sprayers, include: fluid system criteria sensors, such as flow sensors or pressure sensors; sensors indicating which spray head valves or fluid line valves are open; sensors associated with tanks, such as fill level sensors; sectional or system-wide supply line sensors, or row-specific supply line sensors; or kinematic sensors such as accelerometers disposed on sprayer booms. In an embodiment, examples of controllers 114 that may be used with such apparatus include pump speed controllers; valve controllers that are programmed to control pressure, flow, direction, PWM and the like; or position actuators, such as for boom height, subsoiler depth, or boom position.

In an embodiment, examples of sensors 112 that may be used with harvesters include yield monitors, such as impact plate strain gauges or position sensors, capacitive flow sensors, load sensors, weight sensors, or torque sensors associated with elevators or augers, or optical or other electromagnetic grain height sensors; grain moisture sensors, such as capacitive sensors; grain loss sensors, including impact, optical, or capacitive sensors; header operating criteria sensors such as header height, header type, deck plate gap, feeder speed, and reel speed sensors; separator operating criteria sensors, such as concave clearance, rotor speed, shoe clearance, or chaffer clearance sensors; auger sensors for position, operation, or speed; or engine speed sensors. In an embodiment, examples of controllers 114 that may be used with harvesters include header operating criteria controllers for elements such as header height, header type, deck plate gap, feeder speed, or reel speed; separator operating criteria controllers for features such as concave clearance, rotor speed, shoe clearance, or chaffer clearance; or controllers for auger position, operation, or speed.

In an embodiment, examples of sensors 112 that may be used with grain carts include weight sensors, or sensors for auger position, operation, or speed. In an embodiment, examples of controllers 114 that may be used with grain carts include controllers for auger position, operation, or speed.

In an embodiment, examples of sensors 112 and controllers 114 may be installed in unmanned aerial vehicle (UAV) apparatus or "drones." Such sensors may include cameras with detectors effective for any range of the electromagnetic spectrum including visible light, infrared, ultraviolet, near-infrared (NIR), and the like; accelerometers; altimeters; temperature sensors; humidity sensors; pitot tube sensors or other airspeed or wind velocity sensors; battery life sensors; or radar emitters and reflected radar energy detection apparatus; other electromagnetic radiation emitters and reflected electromagnetic radiation detection apparatus. Such controllers may include guidance or motor control apparatus, control surface controllers, camera controllers, or controllers programmed to turn on, operate, obtain data from, manage and configure any of the foregoing sensors. Examples are disclosed in U.S. patent application Ser. No. 14/831,165 and the present disclosure assumes knowledge of that other patent disclosure.

In an embodiment, sensors 112 and controllers 114 may be affixed to soil sampling and measurement apparatus that is configured or programmed to sample soil and perform soil chemistry tests, soil moisture tests, and other tests pertaining to soil. For example, the apparatus disclosed in U.S. Pat. Nos. 8,767,194 and 8,712,148 may be used, and the present disclosure assumes knowledge of those patent disclosures.

In an embodiment, sensors 112 and controllers 114 may comprise weather devices for monitoring weather conditions of fields. For example, the apparatus disclosed in U.S. Provisional Application No. 62/154,207, filed on Apr. 29, 2015, U.S. Provisional Application No. 62/175,160, filed on Jun. 12, 2015, U.S. Provisional Application No. 62/198,060, filed on Jul. 28, 2015, and U.S. Provisional Application No. 62/220,852, filed on Sep. 18, 2015, may be used, and the present disclosure assumes knowledge of those patent disclosures.

2.4. Process Overview-Agronomic Model Training

In an embodiment, the agricultural intelligence computer system 130 is programmed or configured to create an agronomic model. In this context, an agronomic model is a data structure in memory of the agricultural intelligence computer system 130 that comprises field data 106, such as identification data and harvest data for one or more fields. The agronomic model may also comprise calculated agronomic properties which describe either conditions which may affect the growth of one or more crops on a field, or properties of the one or more crops, or both. Additionally, an agronomic model may comprise recommendations based on agronomic factors such as crop recommendations, irrigation recommendations, planting recommendations, fertilizer recommendations, fungicide recommendations, pesticide recommendations, harvesting recommendations and other crop management recommendations. The agronomic factors may also be used to estimate one or more crop related results, such as agronomic yield. The agronomic yield of a crop is an estimate of quantity of the crop that is produced, or in some examples the revenue or profit obtained from the produced crop.

In an embodiment, the agricultural intelligence computer system 130 may use a preconfigured agronomic model to calculate agronomic properties related to currently received location and crop information for one or more fields. The preconfigured agronomic model is based upon previously processed field data, including but not limited to, identification data, harvest data, fertilizer data, and weather data. The preconfigured agronomic model may have been cross validated to ensure accuracy of the model. Cross validation may include comparison to ground truthing that compares predicted results with actual results on a field, such as a comparison of precipitation estimate with a rain gauge or sensor providing weather data at the same or nearby location or an estimate of nitrogen content with a soil sample measurement.

Figure 3:
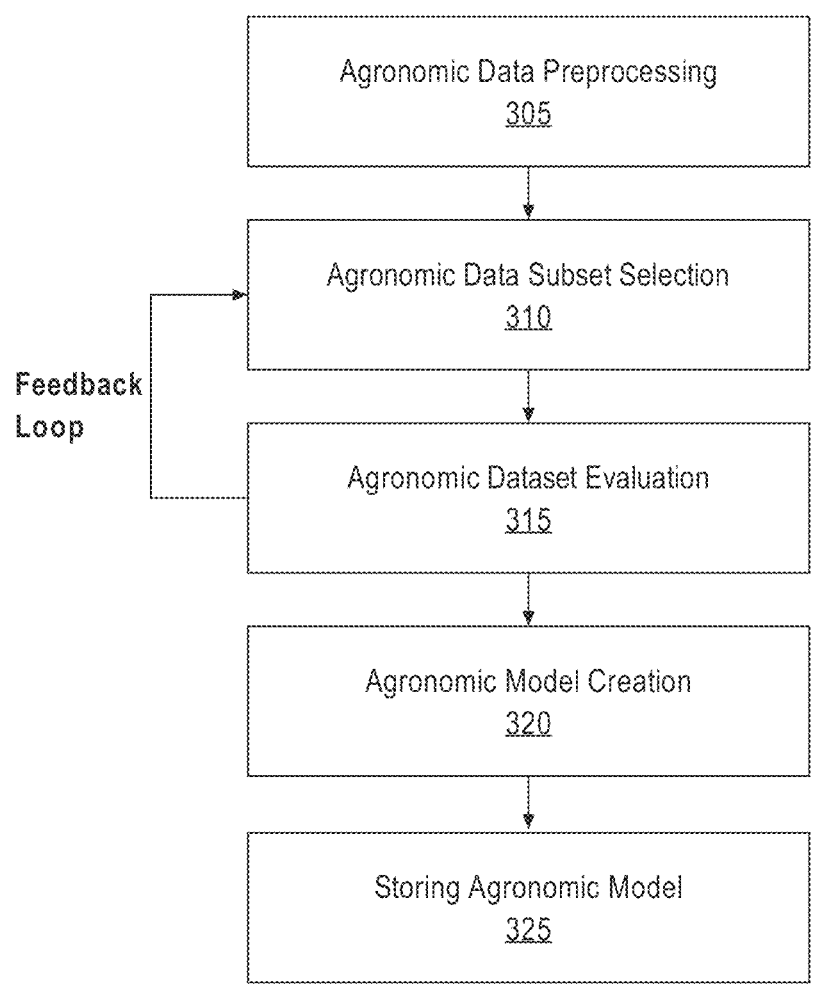
FIG. 3 illustrates a programmed process by which the agricultural intelligence computer system generates one or more preconfigured agronomic models using agronomic data provided by one or more data sources.

FIG. 3 illustrates a programmed process by which the agricultural intelligence computer system generates one or more preconfigured agronomic models using field data provided by one or more data sources. FIG. 3 may serve as an algorithm or instructions for programming the functional elements of the agricultural intelligence computer system 130 to perform the operations that are now described.

At block 305, the agricultural intelligence computer system 130 is configured or programmed to implement agronomic data preprocessing of field data received from one or more data sources. The field data received from one or more data sources may be preprocessed for the purpose of removing noise, distorting effects, and confounding factors within the agronomic data including measured outliers that could adversely affect received field data values. Embodiments of agronomic data preprocessing may include, but are not limited to, removing data values commonly associated with outlier data values, specific measured data points that are known to unnecessarily skew other data values, data smoothing, aggregation, or sampling techniques used to remove or reduce additive or multiplicative effects from noise, and other filtering or data derivation techniques used to provide clear distinctions between positive and negative data inputs.

At block 310, the agricultural intelligence computer system 130 is configured or programmed to perform data subset selection using the preprocessed field data in order to identify datasets useful for initial agronomic model generation. The agricultural intelligence computer system 130 may implement data subset selection techniques including, but not limited to, a genetic algorithm method, an all subset models method, a sequential search method, a stepwise regression method, a particle swarm optimization method, and an ant colony optimization method. For example, a genetic algorithm selection technique uses an adaptive heuristic search algorithm, based on evolutionary principles of natural selection and genetics, to determine and evaluate datasets within the preprocessed agronomic data.

At block 315, the agricultural intelligence computer system 130 is configured or programmed to implement field dataset evaluation. In an embodiment, a specific field dataset is evaluated by creating an agronomic model and using specific quality thresholds for the created agronomic model. Agronomic models may be compared and/or validated using one or more comparison techniques, such as, but not limited to, root mean square error with leave-one-out cross validation (RMSECV), mean absolute error, and mean percentage error. For example, RMSECV can cross validate agronomic models by comparing predicted agronomic property values created by the agronomic model against historical agronomic property values collected and analyzed. In an embodiment, the agronomic dataset evaluation logic is used as a feedback loop where agronomic datasets that do not meet configured quality thresholds are used during future data subset selection steps (block 310).

At block 320, the agricultural intelligence computer system 130 is configured or programmed to implement agronomic model creation based upon the cross validated agronomic datasets. In an embodiment, agronomic model creation may implement multivariate regression techniques to create preconfigured agronomic data models.

At block 325, the agricultural intelligence computer system 130 is configured or programmed to store the preconfigured agronomic data models for future field data evaluation.

2.5. Implementation Example—Hardware Overview

According to one embodiment, the techniques described herein are implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices or any other device that incorporates hard-wired and/or program logic to implement the techniques.

For example, FIG. 4 is a block diagram that illustrates a computer system 400 upon which an embodiment of the invention may be implemented. Computer system 400 includes a bus 402 or other communication mechanism for communicating information, and a hardware processor 404 coupled with bus 402 for processing information. Hardware processor 404 may be, for example, a general purpose microprocessor.

Computer system 400 also includes a main memory 406, such as a random access memory (RAM) or other dynamic storage device, coupled to bus 402 for storing information and instructions to be executed by processor 404. Main memory 406 also may be used for storing temporary variables or other intermediate information during execution of instructions to be executed by processor 404. Such instructions, when stored in non-transitory storage media accessible to processor 404, render computer system 400 into a special-purpose machine that is customized to perform the operations specified in the instructions.

Computer system 400 further includes a read only memory (ROM) 408 or other static storage device coupled to bus 402 for storing static information and instructions for processor 404. A storage device 410, such as a magnetic disk, optical disk, or solid-state drive is provided and coupled to bus 402 for storing information and instructions.

Computer system 400 may be coupled via bus 402 to a display 412, such as a cathode ray tube (CRT), for displaying information to a computer user. An input device 414, including alphanumeric and other keys, is coupled to bus 402 for communicating information and command selections to processor 404. Another type of user input device is cursor control 416, such as a mouse, a trackball, or cursor direction keys for communicating direction information and command selections to processor 404 and for controlling cursor movement on display 412. This input device typically has two degrees of freedom in two axes, a first axis (e.g., x) and a second axis (e.g., y), that allows the device to specify positions in a plane.

Computer system 400 may implement the techniques described herein using customized hard-wired logic, one or more ASICs or FPGAs, firmware and/or program logic which in combination with the computer system causes or programs computer system 400 to be a special-purpose machine. According to one embodiment, the techniques herein are performed by computer system 400 in response to processor 404 executing one or more sequences of one or more instructions contained in main memory 406. Such instructions may be read into main memory 406 from another storage medium, such as storage device 410. Execution of the sequences of instructions contained in main memory 406 causes processor 404 to perform the process steps described herein. In alternative embodiments, hard-wired circuitry may be used in place of or in combination with software instructions.

The term "storage media" as used herein refers to any non-transitory media that store data and/or instructions that cause a machine to operate in a specific fashion. Such storage media may comprise non-volatile media and/or volatile media. Non-volatile media includes, for example, optical disks, magnetic disks, or solid-state drives, such as storage device 410. Volatile media includes dynamic memory, such as main memory 406. Common forms of storage media include, for example, a floppy disk, a flexible disk, hard disk, solid-state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire and fiber optics, including the wires that comprise bus 402. Transmission media can also take the form of acoustic or light waves, such as those generated during radio-wave and infrared data communications.

Various forms of media may be involved in carrying one or more sequences of one or more instructions to processor 404 for execution. For example, the instructions may initially be carried on a magnetic disk or solid-state drive of a remote computer. The remote computer can load the instructions into its dynamic memory and send the instructions over a telephone line using a modem. A modem local to computer system 400 can receive the data on the telephone line and use an infra-red transmitter to convert the data to an infra-red signal. An infra-red detector can receive the data carried in the infrared signal and appropriate circuitry can place the data on bus 402. Bus 402 carries the data to main memory 406, from which processor 404 retrieves and executes the instructions. The instructions received by main memory 406 may optionally be stored on storage device 410 either before or after execution by processor 404.

Computer system 400 also includes a communication interface 418 coupled to bus 402. Communication interface 418 provides a two-way data communication coupling to a network link 420 that is connected to a local network 422. For example, communication interface 418 may be an integrated services digital network (ISDN) card, cable modem, satellite modem, or a modem to provide a data communication connection to a corresponding type of telephone line. As another example, communication interface 418 may be a local area network (LAN) card to provide a data communication connection to a compatible LAN. Wireless links may also be implemented. In any such implementation, communication interface 418 sends and receives electrical, electromagnetic or optical signals that carry digital data streams representing various types of information.

Network link 420 typically provides data communication through one or more networks to other data devices. For example, network link 420 may provide a connection through local network 422 to a host computer 424 or to data equipment operated by an Internet Service Provider (ISP) 426. ISP 426 in turn provides data communication services through the world wide packet data communication network now commonly referred to as the "Internet" 428. Local network 422 and Internet 428 both use electrical, electromagnetic or optical signals that carry digital data streams. The signals through the various networks and the signals on network link 420 and through communication interface 418, which carry the digital data to and from computer system 400, are example forms of transmission media.

Computer system 400 can send messages and receive data, including program code, through the network(s), network link 420 and communication interface 418. In the Internet example, a server 430 might transmit a requested code for an application program through Internet 428, ISP 426, local network 422 and communication interface 418.

The received code may be executed by processor 404 as it is received, and/or stored in storage device 410, or other non-volatile storage for later execution.

3. Functional Description

3.1 Example Processes

Figure 7:
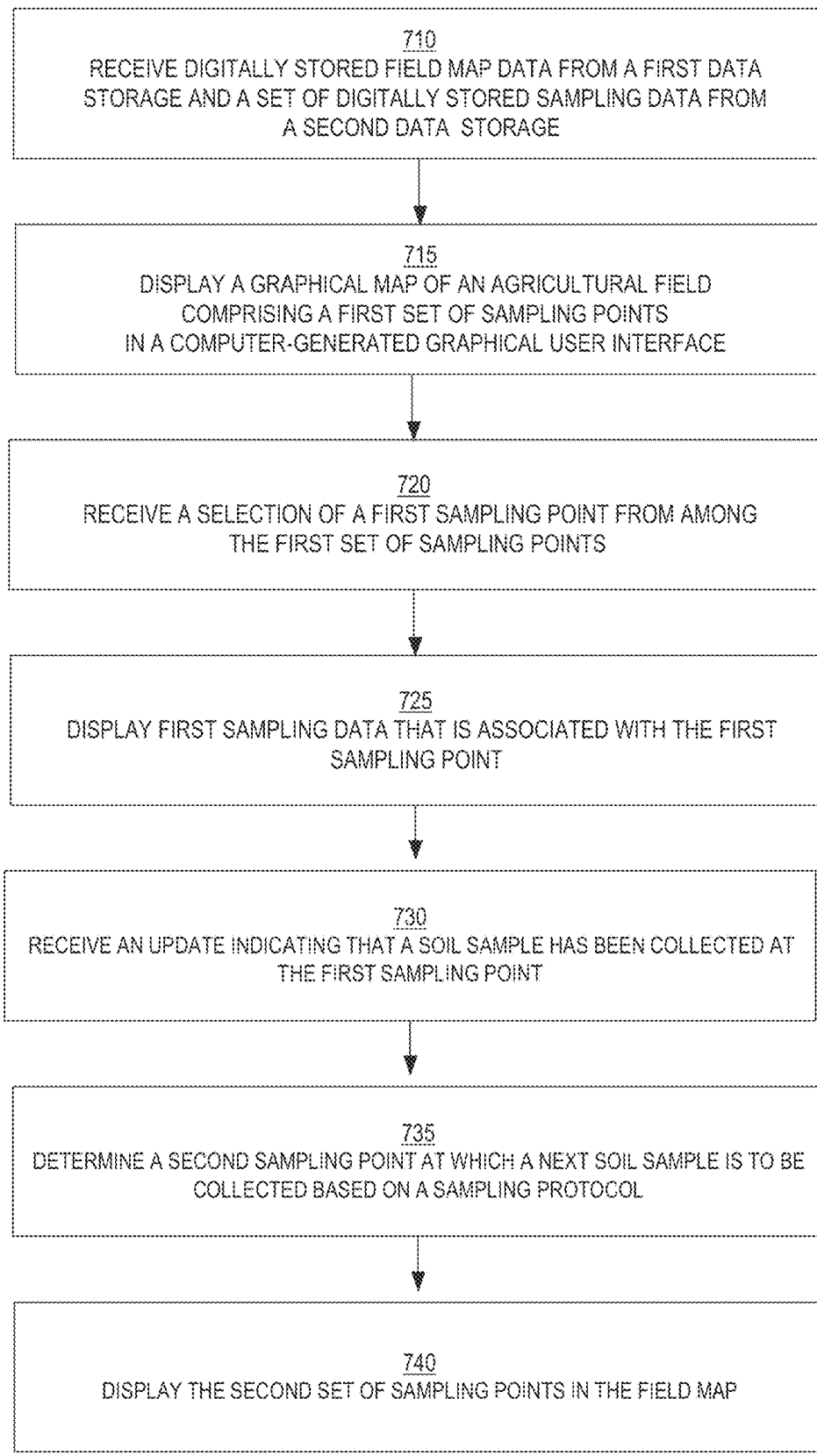
FIG. 7 illustrates an example process for automating soil sampling and tracking soil sampling in a field.

FIG. 7 is an example computer-implemented process for tracking soil sampling in a field. FIG. 7 is intended to disclose an algorithm or functional description that may be used as a basis of writing computer programs to implement the functions that are described herein, and which cause a computer to operate in the new manner that is disclosed herein. Further, FIG. 7 is provided to communicate such an algorithm at the same level of detail that is normally used, by persons of skill in the art to which this disclosure is directed, to communicate among themselves about plans, designs, specifications and algorithms for other computer programs of a similar level of complexity.

In an embodiment, a request for a field map may be received via a computer-generated graphical user interface of the field manager computing device 104. A collector may create an order for a field map by inputting a field identification or geographic coordinates associated with the field map. The field map includes one or more sections that are delineated based on agricultural characteristics or geographic coordinates of the field. For example, the field map may include geographical coordinates of one or more sections, distance information to a boundary of one or more sections, or a set of agricultural characteristic values for one or more sections in the field map. Each section may be assigned to a corresponding sampling point which can be represented by a pin or an icon. Each sampling point can be numbered according to the geographic coordinates of the sections or one or more sampling protocols stored in the model data field data repository 160.

At step 710, the process receives digitally stored field map data from a first data storage and digitally stored sampling data from a second data storage. In some embodiments, the first data storage can be associated with a third-party satellite imagery provider. The second data storage can be associated with a testing facility or a laboratory. The field map can be a two-dimensional (2D) or a three-dimensional (3D) representation of satellite imaginary and may include geospatial data of one or more fields for soil testing to determine nutrient content, composition, and other characteristics. The field map can include field information such as a farm location and size, a grower, crops, or crop yield. The set of sampling data can include soil physical characteristics such as pH level, acidity, macronutrients, or micronutrients. The set of sampling data can also include topological characteristics such as soil type, soil depth, drainage information, or soil size.

At step 715, based on the field map data and the sampling data, a graphical map of the agricultural field is caused to be displayed in the computer-generated graphical user interface. The field map includes a first set of sampling points that is represented by a set of corresponding pins or icons as shown in FIG. 9B. In some embodiments, each sampling point can be separated by a minimum distance based on various distance constraints or field delineation algorithm.

At step 720, the process receives a selection of a first sampling point from among the first set of sampling points. The selection can be made by selecting the corresponding pin or clicking anywhere within the boundary of the corresponding section in the field map. In some embodiments, the first set of sampling points can be user-designated sampling points.

At step 725, sampling data for the selected first sampling point is displayed in the graphical user interface. As shown in FIG. 9B, the first sampling data includes a set of agricultural characteristics and a set of order data. The set of agricultural characteristics can include soil physical attributes such as field information, farm information, or yield information. The order data can include logistic attributes such as a sampled date, a shipment date, a collector identification, or a sampling protocol.

After the collector collects a soil sample at the first sampling point, the collector can update the order data by updating the sampled data or the shipment data. At step 730, when the collector updates the order data, the process receives an update indicating that a soil sample has been collected at the first sampling point. The order data can be updated to reflect the correct sampled date or the shipment date. The updated sampling data can be stored in the model data field data repository 160.

In some embodiments, upon receiving the update that the soil sample has been collected, a new graphical user interface showing one or more available testing facilities that are linked to the field can be displayed. Laboratory data identifying one or more available testing facilities may be retrieved. In some embodiments, the laboratory data may be linked to the field map. The testing facilities can test the soil samples and sampling data can be retrieved from the selected testing facility. The collector can select any available testing facility to send a soil sample that meets the testing criteria.

In another embodiment, a different user interface showing one or more available shipping carriers may also be displayed. The shipping carriers are capable of shipping the soil samples to the selected testing facility. The shipping carriers can be determined based on at least one of the distance information, pick-up availability, time information, or pricing information. The shipping carriers can be ranked based on such information and presented in the graphical user interface.

In one embodiment, the field manager computing device 104 can be connected to a peripheral computing device that prints a tag for the soil sample. The tag includes an identification code that matches with the updated sampling data that is stored in the model data field data repository 160. The tag may include details of the sampling data such as an order number, sampled date, shipment data, collector identification, or field identification. The tag can be affixed to the soil sample or the soil sample bag for accurate delivering of the soil sample.

In some embodiments, the peripheral computing device can be a wireless printing device that can print labels for soil bags that hold the samples. In an embodiment, the processor can generate a Quick Response (QR) code that includes a matrix barcode that can be read by the peripheral computing device and the field manager computing device 104. The tag or the QR code can be sent to the selected testing facility and the selected shipping carrier for tracking the soil sample.

At step 735, the process determines a second sampling point at which a next soil sample can be collected. In some embodiments, determining the second sampling point can be based on the geographic coordinates of the sections or the sampling protocol. For example, the processor can determine an adjacent sampling point to the first sampling point for efficient soil sampling. Similarly, the processor can determine the next sampling location based on the sampling data received from the testing facility.

At step 740, the second sampling point can be displayed in the field map. The second sampling point is depicted using visually different attributes compared to the first sampling point. For example, a collected sampling point (e.g., highlighted in red) can be visually distinguished from an uncollected sampling point (e.g., highlighted in green) in the field map.

Figure 8A:
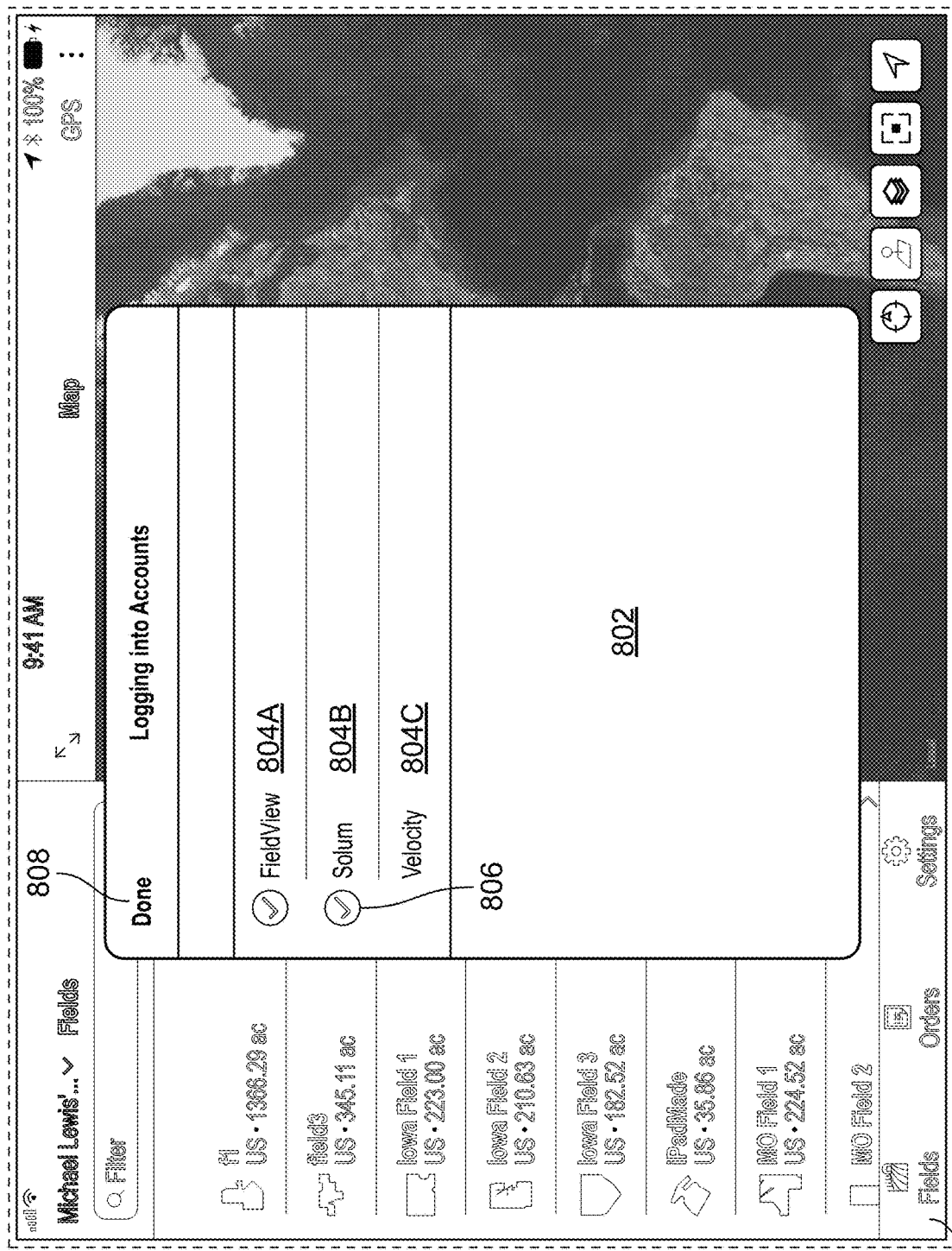
FIG. 8A, FIG. 8B, and FIG. 8C are screen snapshots of example computer-generated graphical user interfaces configured to create an order for soil sampling.
Figure 8B:
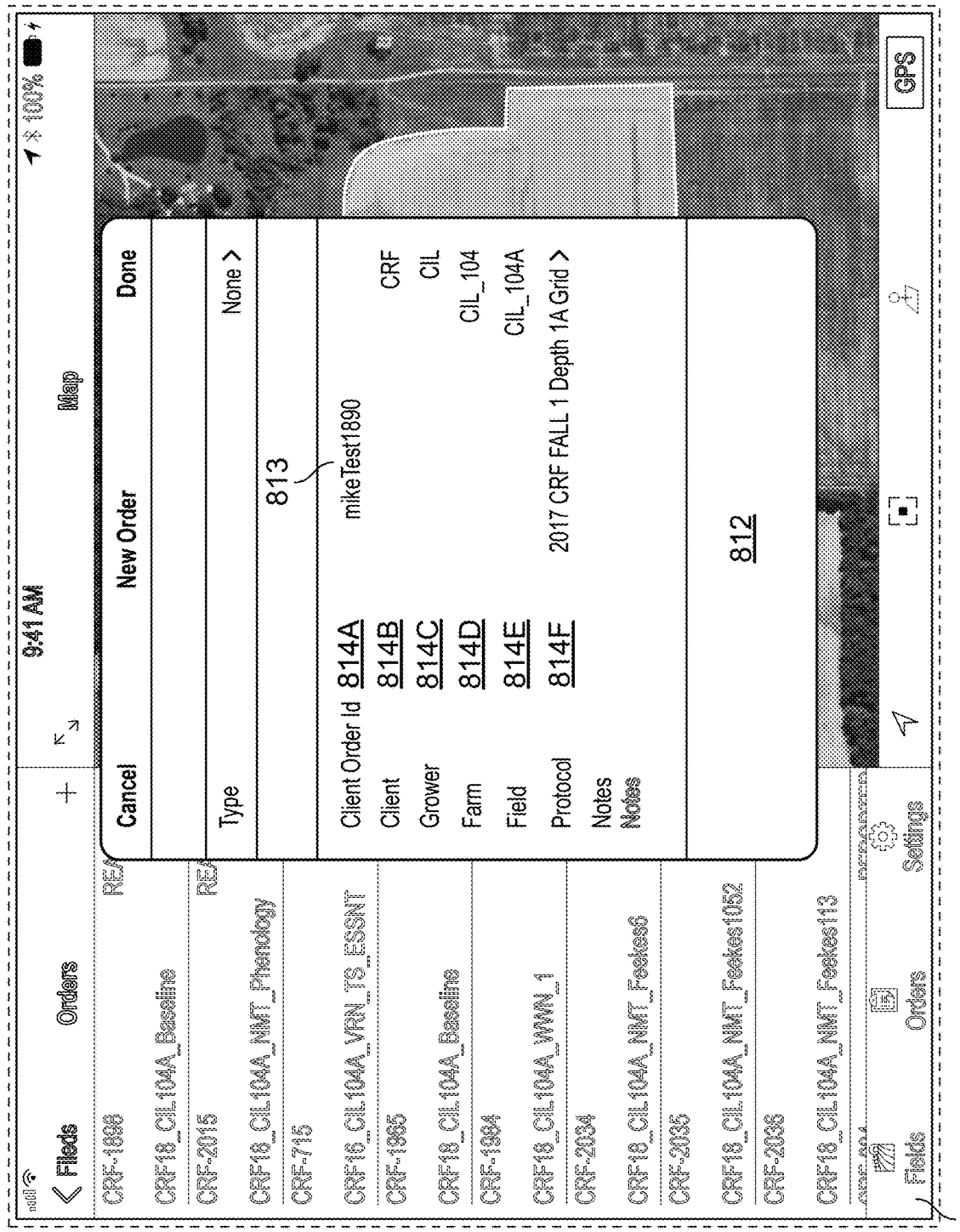
Figure 8C:
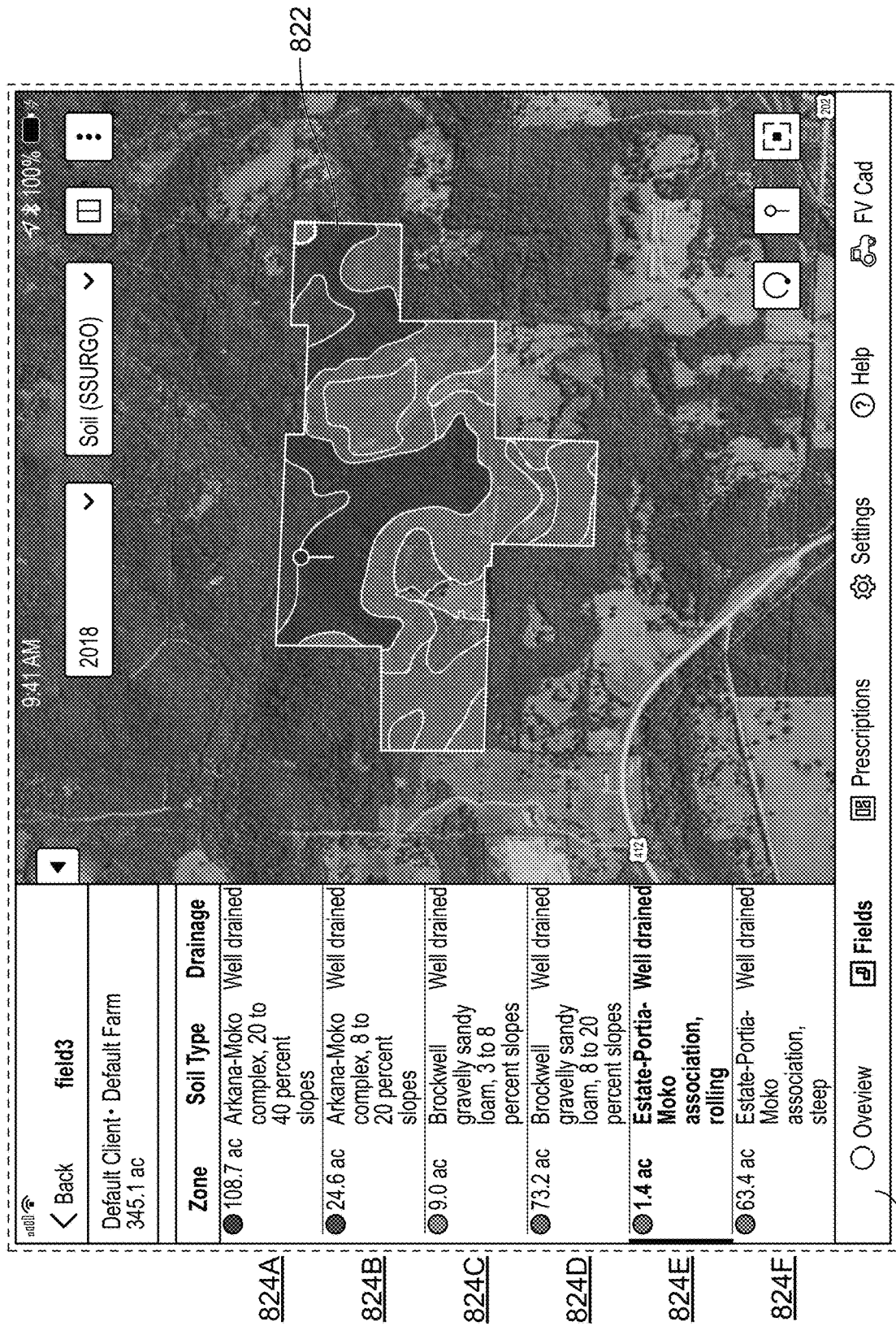

4. Example Computer-Generated Graphical User Interfaces 4.1 Generating an Order for Soil Sample and Selecting the Field FIG. 8A, FIG. 8B, FIG. 8C are screen snapshots of example computer-generated graphical user interfaces configured to generate an order and select a field. In this disclosure, the term "screen snapshot" refers to a reproduction of all or part of an example graphical user interface that may form output of programs or other software elements that have been programmed to implement the functions that are described herein. Graphics libraries and other utility programs that can be called or incorporated into such programs are considered within the knowledge of a person of skill to which this disclosure is directed. Therefore, this disclosure presents examples of graphical output in the form of the screen snapshots because these examples will fully inform a skilled person about what output is desired and that the skilled person will be capable of determining the specific programming needed to cause a computer to reproduce the output that is shown, based on the drawing figures, their accumulated skill and the specific functional information that is provided in the following sections.

Each example screen snapshot may be generated by executing instructions that provide interactivity between a collector, or a computer of the collector, and an application or a web browser displayed on the field manager computing device 104. A typical user of the application is a collector or a lab technician who collects a soil sample. Executing the instructions may allow a collector and their computer to import and export certain information about an agricultural field to the application. Executing the instructions may also allow a collector computer to request an interactive tool that would allow the collector to define the sampling points and display and update the sampling data in the graphical user interface.

For example, the collector may log into the application or the web browser on the field manager computing device 104 using user credentials to see a field map of interest. The user credentials may be associated with a specific collector which may be associated with a particular sample protocol related to the specific field and the sampling data.

FIG. 8A is a screen snapshot of an example computer-generated graphical user interface for searching for a testing facility on a log-in page. In an embodiment, a screen display 800 may comprise a pop-up account selection window 802 comprising a plurality of selectable rows 804A, 804B, 804C each associated with a different testing facility or laboratory. In an embodiment, each row 804A, 804B, 804C comprises a selection widget 806 that is responsive to input via a pointing device such as mouse, trackball or keyboard. In an embodiment, input selecting a widget 806 causes recording data to select a laboratory of the associated row and to update the window 802 to include a check mark to signal that the row is selected. Each widget 806 may be implemented as a toggle such that repeated selection causes removal of a selection. Each testing facility or laboratory can maintain a database for one or more fields and provide field map data and sampling data when a request for the sampling data is received. Window 802 further comprises a Done graphical button 808 or hyperlink which when selected causes closing the window and transitioning the user interface to a different state.

FIG. 8B is a screen snapshot of an example computer-generated graphical user interface for creating an order. The collector may be presented with a new interface that displays the order details that allows the collector to select a field of interest. In an embodiment, a screen display 810 may comprise a pop-up order creation window 812 comprising a plurality of rows 814A, 814B, 814C, 814D, 814E, 814F, each associated with order details. The example order details can include client order identification 814A, client identification 814B, grower information 814C, farm information 814D, field information 814E, or sampling protocol information 814F. In an embodiment, each row 814A, 814B, 814C, 814D, 814E, 814F comprises an input field 813 in which the collector can type particular order details. For example, the collector may input specific field information by entering the field identification or field geographic coordinates. In another embodiment, the collector can simply click an order that is associated with the collector credentials. For instance, each input field may auto-populate one or more order details (e.g., grower type, farm type) that is responsive to input via an input device. One or more order details can be determined based on the sample protocol associated with the collector identification. The multiple input fields cause recording data to select a single order based on the input provided by the collector.

In some embodiments, an order that a first collector creates can be exported to a second collector who is at a remote location. The order data can be synced with the second collector account that is associated with a third-party sample collection organization that can be different from a sample collection organization associated with the first collector.

FIG. 8C is a screen snapshot of an example layout of a field. In an embodiment, a screen display 820 may comprise a zone map 822 and a list of a plurality of zones 824A, 824B, 824C, 824D, 824E, 824F associated with the zone map 822. The zone map 822 can be a computer-generated graphical map of an agricultural field. Each zone can be delineated based on the Soil Survey Geographic Database (SSURGO) zone layers. The SSURGO layer adds satellite imagery with nutrient information such as nitrogen, boron, calcium information. In addition to the SSURGO information, the layout may include agricultural characteristics such as a soil type (e.g., Arkana-Moko complex), drainage information (e.g., well drained), or a size of the zone (e.g., 73.2 acres). Each boundary can define a zone that is differentiated from other zones in the field map based on the agricultural characteristics or geographic coordinates.

4.2 Soil Sampling

Figure 9A:
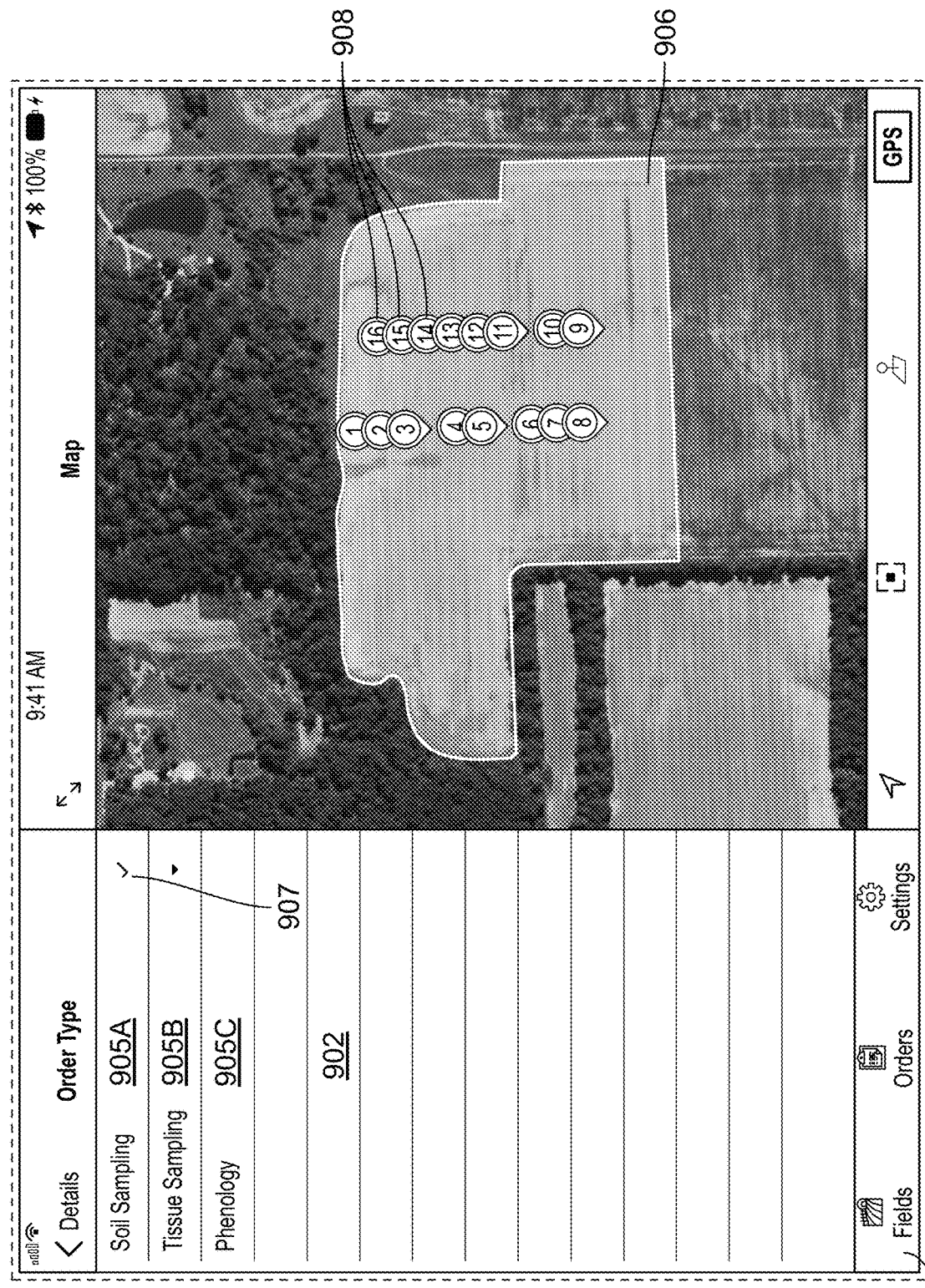
FIG. 9A, FIG. 9B, FIG. 9C, and FIG. 9D are screen snapshots of example computer-generated graphical user interfaces for soil sampling.
Figure 9B:
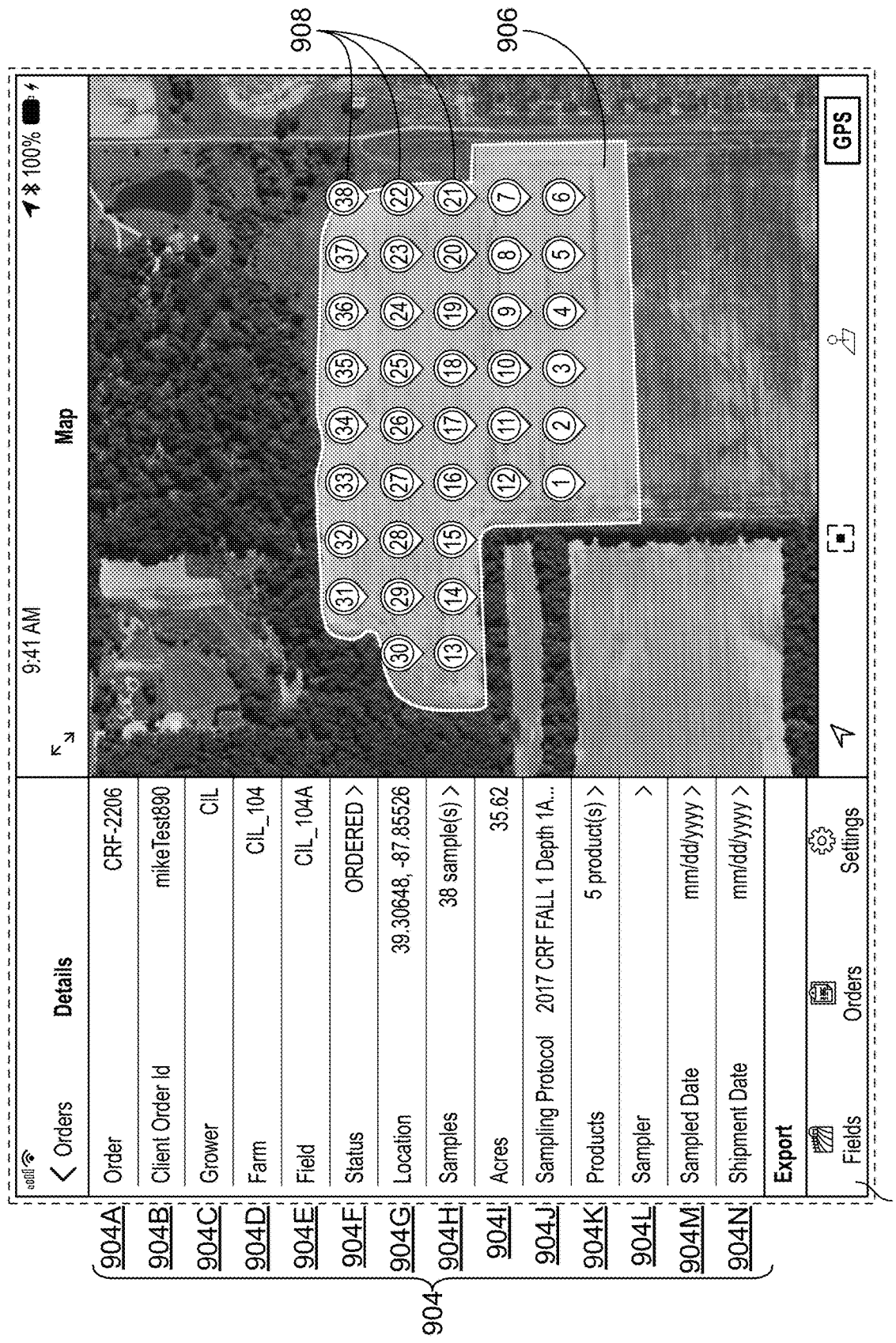

FIG. 9A is a screen snapshot of an example computer-generated graphical user interface for selecting an order type for sampling. In an embodiment, a screen display 900 may comprise an order selection window 902 comprising a plurality of selectable rows 905A, 905B, 905C, each associated with a different order type. In an embodiment, each row 905A, 905B, 905C comprises a selectable widget 907 that is response to input via a pointing device. In an embodiment, input selecting widget 907 causes recording data to select an order type of the associated row and to update the window 902 to include a check mark to signal that the row is selected. Each widget 907 may be implemented as a toggle such that repeated selection causes removal of a selection.

The example interface shows three examples of soil sampling order types: 1) soil sampling; 2) tissue sampling; and 3) phenology sampling; however, the approach is not limited to three examples. Upon receiving a selection from the collector (e.g., soil sampling), the processor is programmed to display a field map 906 including a first set of sampling points 908 and sampling data as illustrated in FIG. 9B.

FIG. 9B is a screen snapshot of an example computer-generated graphical user interface for displaying a field map and sampling data. A screen display 910 may comprise field map data comprising a field map 906 with a plurality of sampling points 908 and sampling data comprising a plurality of rows 904A, 904B, 904C, 904D, 904E, 904F, 904G, 904H, 904I, 904J, 904K, 904L, 904M, 904N, each row is associated with different sampling data. In an embodiment, the field map can be a computer-generated graphical map of an agricultural field that may comprise a set of sampling points. The sampling data can be a set of agricultural properties that can be retrieved from the second data source or updated by the collector. For example, the sampling data may include an order name 904A, client order id 904B, grower information 904C, farm identification 904D, field identification 904E, order status 904E, location information 904G, sample information 904H, size information 904I, sampling protocol information 904J, product information 904K, sampler information 904L, sampled date 904M, and shipment date 904N; however the sampling data is not limited to the listed examples. In some embodiments, the field map data and the sampling data may be retrieved from the first data source or the second data source and further can be updated by the collector.

In some embodiments, the first set of sampling points 908 can be defined subject to various distance constraints, such as having two sampling points separated by a minimum distance. For example, a set of equidistant sampling points or a set of quarter acre size sampling points may be identified for a first set of sampling points. Defining the sampling points is further described in other sections herein.

In one embodiment, a new set of sampling points can be assigned by the collector. The collector may specify the best n number of ways of dividing a particular field into sampling points. For example, the user interface may provide the geographical configuration that allows the collector to set a new set of sampling points (e.g., a second set of sampling points) that can be different from the pre-defined sampling points (e.g., a first set of sampling points). Accordingly, the geographic coordinates of the first set of sampling points can be different from the geographic coordinates of the second set of sampling points.

The processor is programmed to receive user input to assign the second set of sampling points to one or more sections designated by the collector. The second set of sampling points can be renumbered corresponding to the geographical coordinates of the field map. In some embodiments, renumbering can be performed based on a sampling protocol stored in the model and field data repository 160. In some instance, the collector may request to replace the first set of sampling points with the second set of sampling points. Upon receiving a replacement request from the collector, the second set of sampling points can be replaced with the first set of sampling points in the field map.

In some embodiments, a physical location of the collector or the field manager computing device 104 can be identified using the GPS tracking system and a corresponding sampling point can be determined based on the geographical coordinates. The detected location can be displayed in the graphical user interface as a current location of the collector by dropping a pin in the field map. In some embodiments, the collector may be presented with a 'my location' tab and can simply click on the 'my location' tab to determine a physical location in the field map.

In another embodiment, a designation of the desired particular sampling location can be made in the field map. For example, the collector can simply press and hold, and drop a new pin at anywhere in the field map. The designated sampling location can be displayed as a distinctive pin the field map for easy reference.

In one instance, pins for the uncollected sampling points can be removed from the field map. For example, the processor may provide navigation functionality with the pins that allow the collector to move existing uncollected sampling point pins with a simple press and hold gesture on the graphical user interface. In another embodiment, the interface further provides removal functionality that the uncollected sampling points can be deleted from the field map with a user-designated gesture on the user interface.

In some embodiments, the numbering of sampling points can be performed concurrently with the collection process. For example, the processor may display the field grid without numbering the sampling points. As the collector collects samples and updates the sampling data, corresponding sampling points can be numbered concurrently. This allows the collector to identify the collected sample locations and further identify uncollected sample locations in the field map.

In one embodiment, the processor is configured to determine a next sampling location (e.g., second sampling point). After a soil sample is collected at the first sampling location, the processor determines a second sampling point based on the sampling protocol information stored in the model and field data repository 160 or geographical information of the first sampling location. The location of the second sampling point can be compared with location information displayed in the cab computer 115 to verify a correct sampling location for the second soil sample.

Figure 9C:
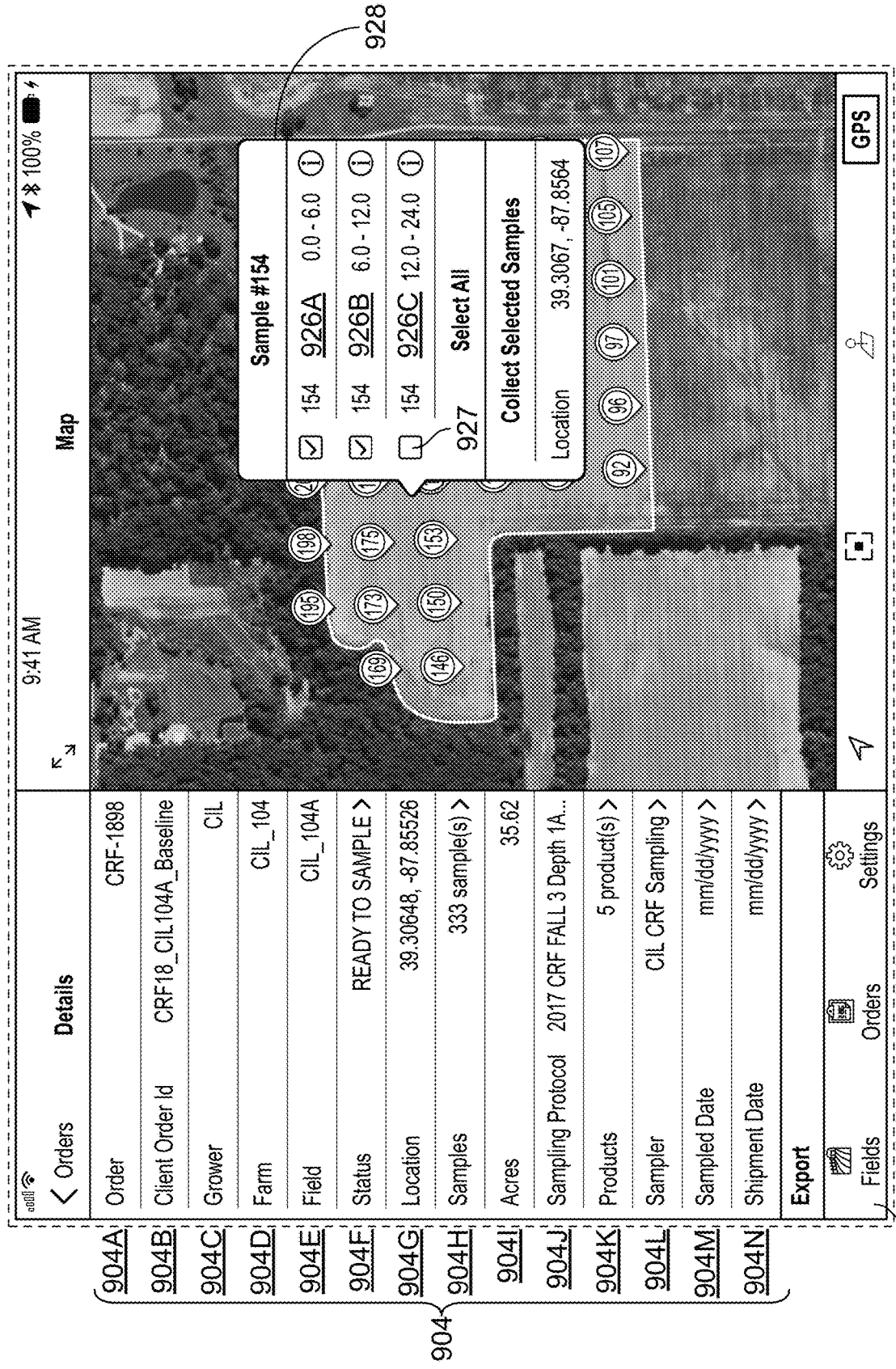

FIG. 9C is a screen snapshot of an example computer-generated graphical user interface for sampling at different depths. In an embodiment, a screen display 920 may comprise a pop-up sample window 928 comprising a plurality of selectable rows 926A, 926B, 926C, each associated with a different layer of a sampling point. The example interface shows three example sampling layers at different depths—1) zero to six inches from a surface level 926A; 2) six inches to twelve inches from the surface level 926B; and 3) twelve inches to twenty-four inches from the surface level 926C; however, the approach is not limited to three sampling layers. Different layers may include different nutrients that can have different effects on the plants. For example, the nitrogen level or moisture level can vary for different layers and it is important to know the accurate content of each nutrient because the roots can go down to as long as six inches to a foot.

Each row 926A, 926B, 926C comprises a selection widget 927 that is responsive to input via an input device. In an embodiment, input selecting the widget 927 causes recording data to update the window 928 to include a check mark to signal that the row is selected. Each widget 928 may be implemented as a toggle such that repeated selection causes removal of a selection. When the sampling at a first layer is performed, the collector may check a box for the first layer which can prompt the processor to display the collected sample layer visually differently from uncollected sample layers. For example, the processor is configured to highlight the collected sampling point or layer using visually different attributes compared to the uncollected sampling points or layers. The changes can be displayed in the field map and the sample window 928. In some embodiments, a set of sampling data 904 may still be shown in the screen display 920 to display the information of the sampling point. Upon completion of soil collection, the processor is configured to update the sampling data 904, display the updated data in the screen display 920, and store the updated sampling data in the database.

Figure 9D:
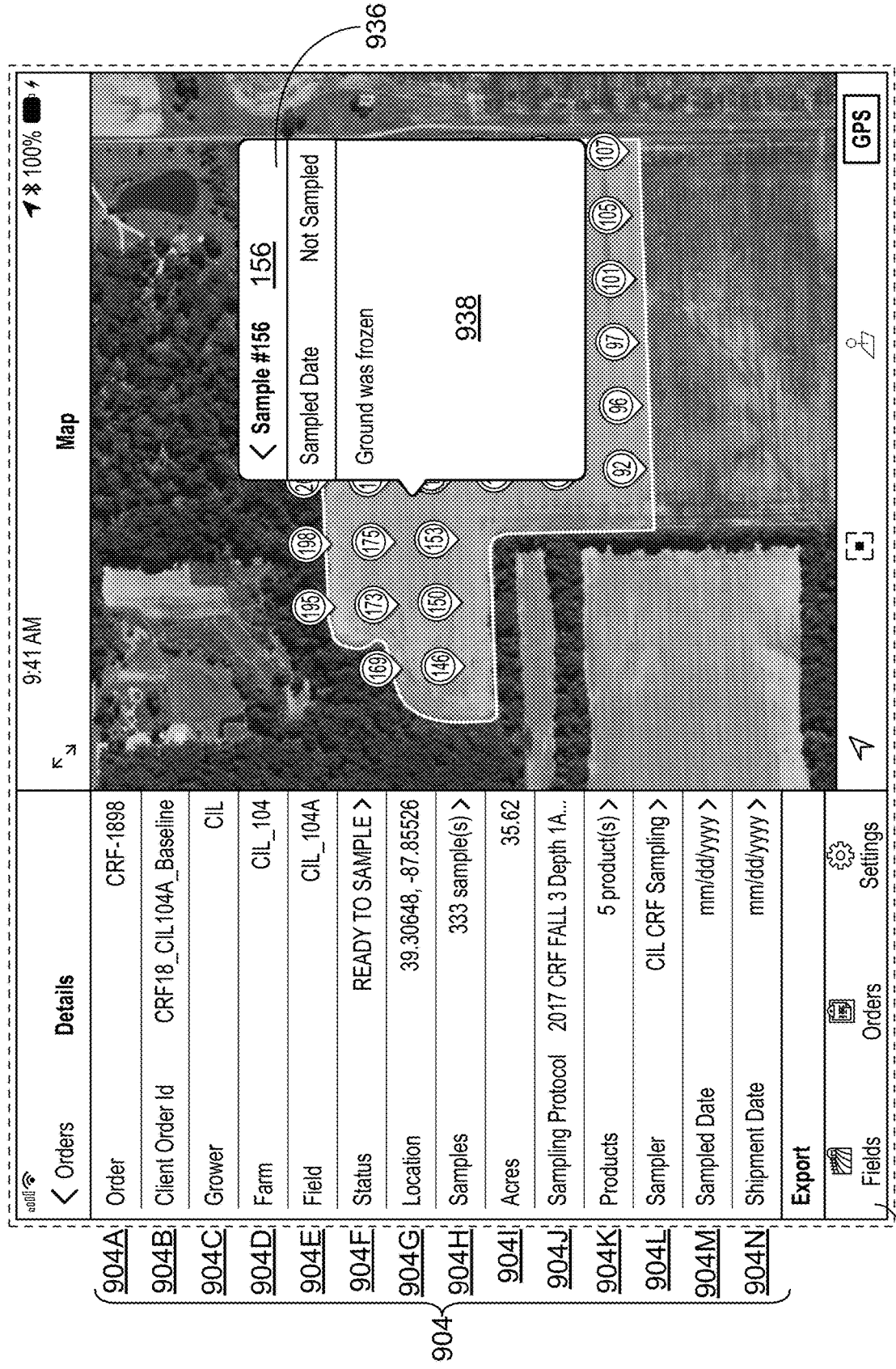

In the example of FIG. 9D, when the collection is unavailable, the collector can specify the reasons why the collection was unsuccessful (e.g., the ground was frozen). In an embodiment, a screen display 930 may comprise a set of sampling data 904 and a pop-up note window 936 identifying a particular sample point and may comprise a note field 938. The note window 936 is responsive to an input device such as keyboard, mouse, or touchpad. Using the input device, the collector may provide sample details such as why sample collection was unavailable or any specific details to note regarding soil sampling of the particular sampling point. This can help more accurate test results and allow the collector to collect the soil samples at a later time. In some embodiments, when the collector inputs the collection details, the SI unit measurement (e.g., metric systems v. US standard system) can be compatible and consistent with the standard industry or the sampling protocol to avoid data irregularities and to ensure persistent and predictable results.

4.3 Tissue Sampling and Phenology Sampling

Figure 10A:
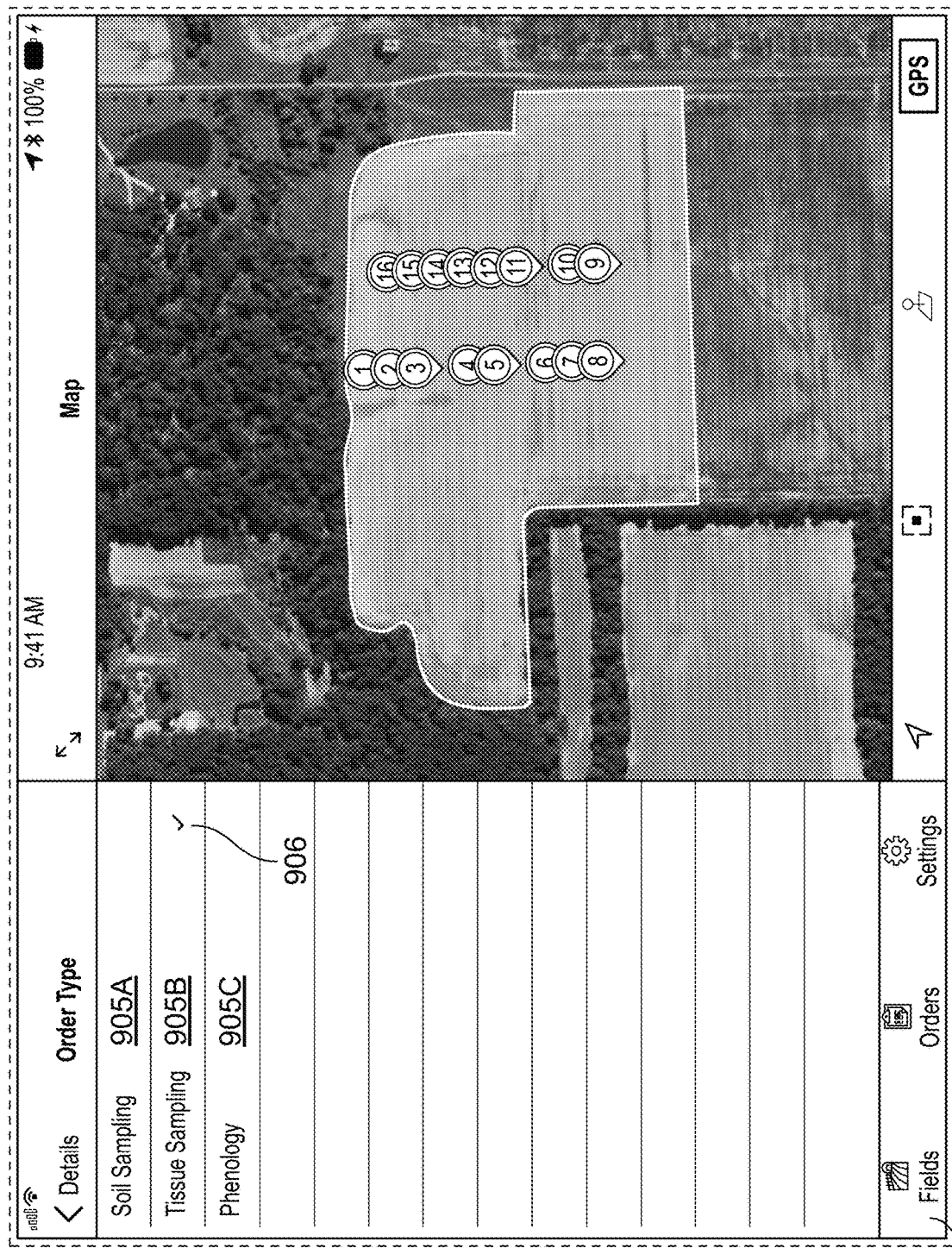

FIG. 10A is a screen snapshot of an example computer-generated graphical user interface configured to select an order type (e.g., tissue sampling). Similar to the screen display 900 of FIG. 9A, a screen display 1000 may comprise a plurality of selectable rows 905A, 905B, 905C, each associated with a different order type. The screen display 1000 may also comprise the selection widget 906 that when selected, a selection of the order type can be removed. The collector may select an order type (e.g., tissue sampling) by clicking an order type of the associated row as shown in FIG. 10A.

Figure 10B:
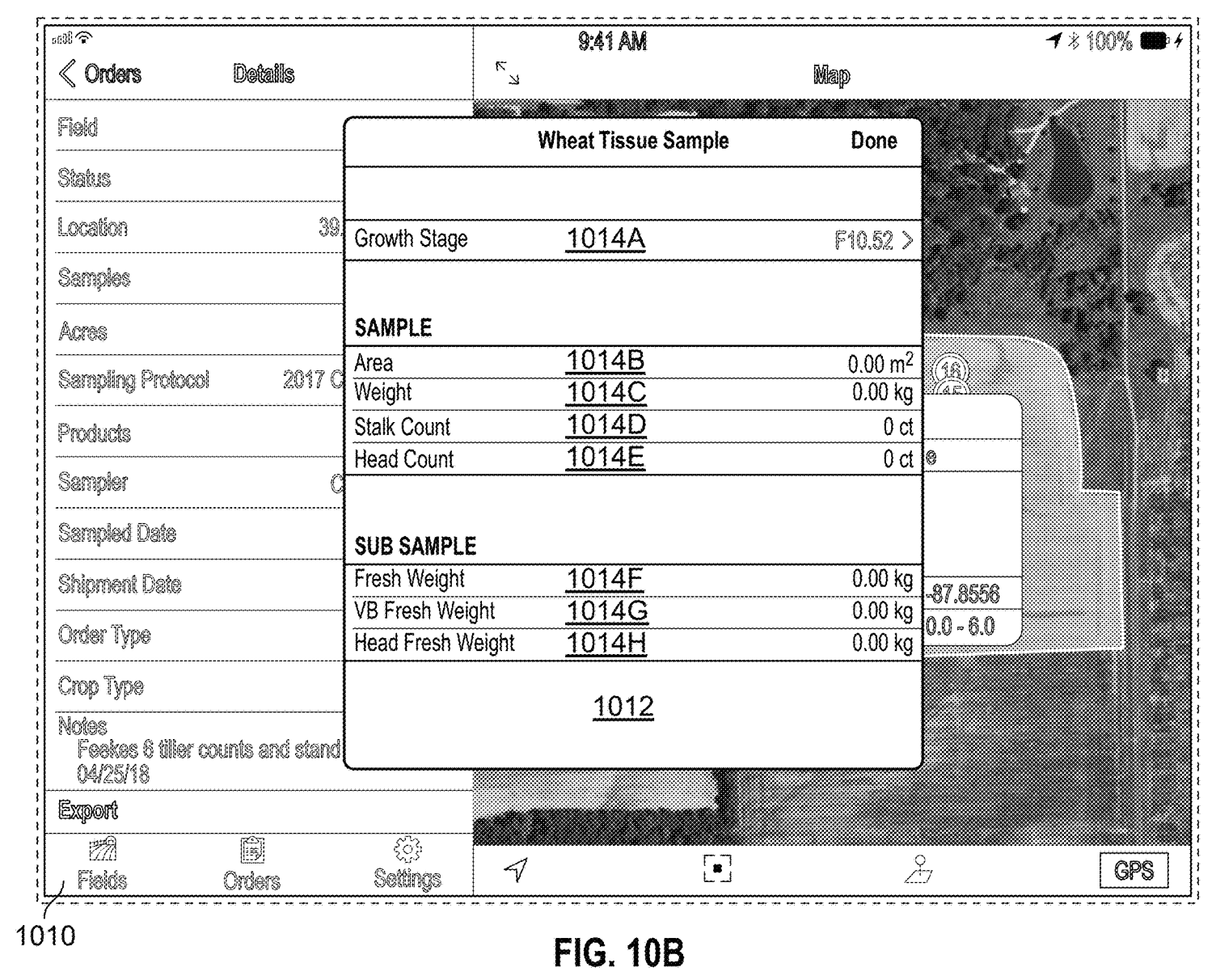

In the example of FIG. 10B, the tissue sampling data may include sampling data that is different than the soil sampling data. In an embodiment, a screen display 1010 may comprise a pop-up tissue sample window 1012 comprising a plurality of rows 1014A, 1014B, 1014C, 1014D, 1014E, 1014F, 1014G, 1014H, each associated with different tissue sampling data. For example, the tissue sampling data can include information such as growth stage 1014A, sample area 1014B, sample weight 1014C, stalk count 1014D, headcount 1014E, fresh weight 1014F, VB fresh weight 1014G, or head fresh weight 1014H.

Figure 10C:
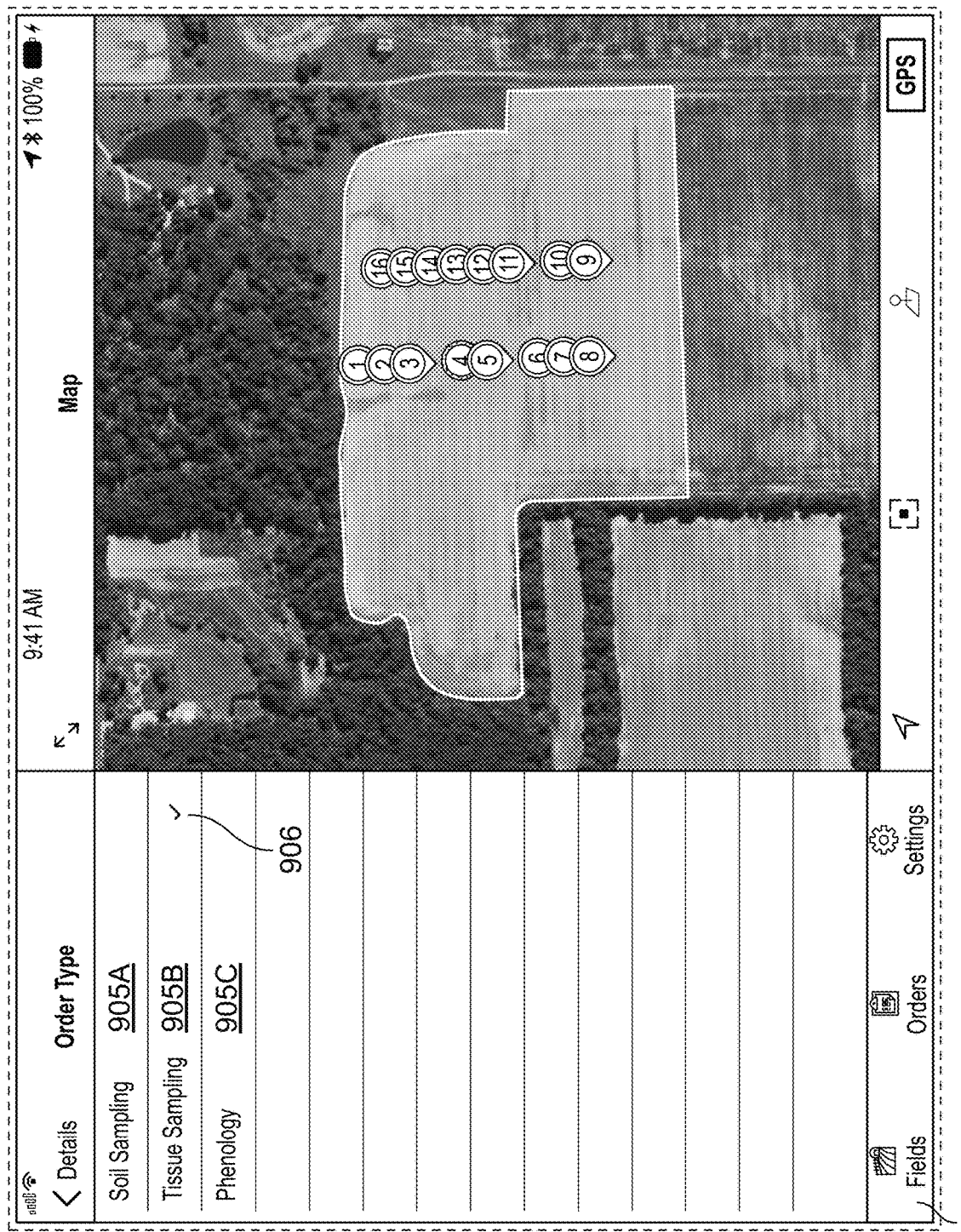

FIG. 10C is a screen snapshot of an example computer-generated graphical user interface configured to select an order type (e.g., phenology sampling). Similar to the screen displays 900, 1000 of FIG. 9A and FIG. 10A, a screen display 1020 may comprise a plurality of selectable rows 905A, 905B, 905C, each associated with a different order type. The screen display 1000 may also comprise the selection widget 906 that when selected, a selection of the order type can be removed. The collector may select an order type by clicking an order type of the associated row (e.g., phenology sampling) as shown in FIG. 10C.

Figure 10D:
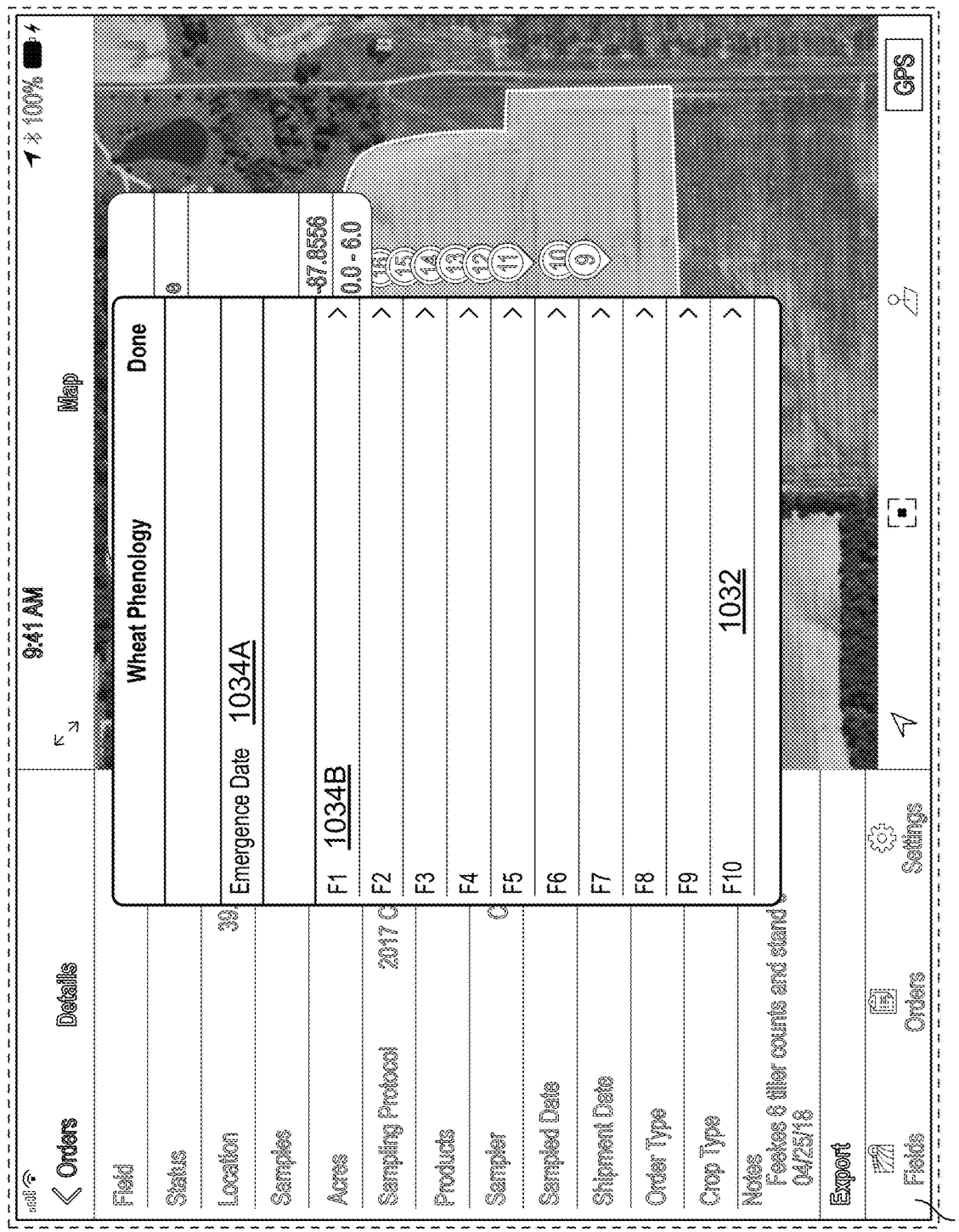

In the example of FIG. 10D, the phenology sampling data may include sampling data that is different than the soil sampling data or tissue sampling data. In an embodiment, a screen display 1030 may comprise a pop-up phenology sample window 1032 comprising a plurality of rows 1034A, 1034B, each associated with different phenology sampling data. For example, the phenology sampling data can include information such as an emergence date 1034A.

4.4 Generating a Tag for Soil Sample and Sampling Data

Figure 11:
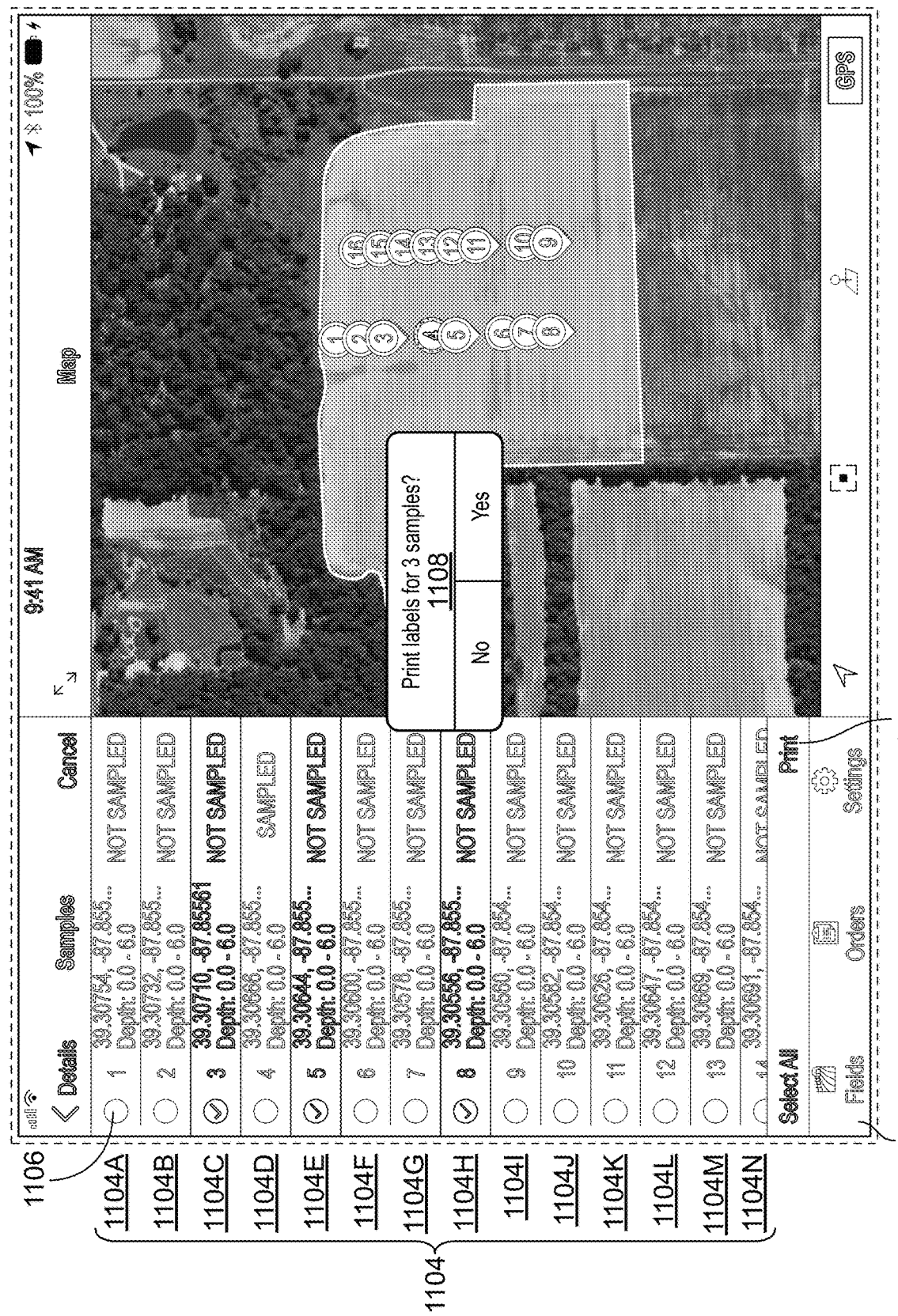
FIG. 11 is a screen snapshot of an example computer-generated graphical user interface configured to generate a tag for a soil sample and sampling data.

FIG. 11 is a screen snapshot of an example computer-generated graphical user interface for generating a label (e.g., tag) for the soil sample and the sampling data. Upon completing the soil collection, the collector may be presented with a printing interface and can select a printing option to print the labels for soil bags using the printing device. In an embodiment, a screen display 1100 may comprise a selection window 1104 comprising a plurality of selectable rows 1104A, 1104B, 1104C, 1104D, 1104E, 1104F, each associated with a different sampling point. In an embodiment, each row 1104A, 1104B, 1104C, 1104D, 1104E, 1104F comprises a selection widget 1106 that is responsive to input via a pointing device. In an embodiment, input selecting the widget 1106 causes recording data to select a sampling point of the associated row and to update the window 1104 to include a check mark to signal that the row is selected. Each widget 1106 may be implemented as a toggle such that repeated selection causes removal of a selection.

In an embodiment, sampling data of the selected sampling points can be transmitted to the printing device. In an embodiment, the screen display 1100 may comprise a print button 1102 that causes recording data to transmit the sampling data of the selected sampling points to the printing device. The print button 1102 is responsive to input via the printing device and input selecting the print button 1102 causes recording data to generate a pop-up printing window 1108. Upon selecting a Yes button in the printing window 108, sampling data is sent to the printing device to print the label. The transmitted sampling information may include any identifiable information to verify a correct sample such as a sampled date, collector information, sampling point identification, field identification or collector identification. In some embodiments, the field manager computing device 104 may generate a barcode type identification (e.g., QR code) and the printing device can print a label with the QR code that can be scanned at the testing facility.

For verification, the sampling information of the label can be matched with the sampling information stored in the database. The processor is configured to store the sampling data in a database that is shared with a respective testing facility. The collector may be presented with one or more available testing facilities to transmit the sampling data. The testing facilities can be selected based on various factors such as pricing information, distance information or testing availability of each testing facility. Upon receiving a selection on the testing facility via the computer-generated graphical user interface, the processor is configured to transmit the updated sampling data to the testing facility over the network. The label information can be shared with the selected testing facility and the transmitted sampling data can be compared with the label of the soil bag. Printing the label using the printing device system can minimize the human mistakes that can be caused by inconsistent handwriting.

In some embodiments, the processor is configured to determine one or more available shipping carriers that are linked to the field. The processor may import shipping logistics and travel routes to the selected testing facility from one or more shipping carriers. The processor may further rank the shipping carriers based on the received information and present the shipping carrier options based on the ranked order. The processor is configured to receive a selection on the shipping carrier from the collector via the computer-generated graphical user interface and transmit the shipping carrier information to the testing facility over the network. This may facilitate fast handling of the soil samples as the soil chemistry can change over time.

5. Extensions and Alternatives 5.1 Normalizing or Weighting Agricultural Characteristic Values In an embodiment, the first set of sampling points can be based on the weighted algorithm for the agricultural characteristics of the field. For example, the server is programmed to normalize values of each agricultural characteristic to reconcile different units used for a single agricultural characteristic and to unify the scales of all the agricultural characteristics. Specifically, the server can convert each agricultural characteristic value into a quotient of the difference from the global minimum value for the agricultural characteristic to the global range. In other words, the scaled vector $\tilde{Z}_{S_j}$ of agricultural characteristic values for a candidate sampling location and the scaled vector $\tilde{Z}_{O_j}$ of model values used by an agricultural modeling tool can be computed as follows:

$$\tilde{Z}_{S_j} = \frac{z_{S_j} - z_{j_{min}}}{z_{j_{max}} - z_{j_{min}}}; \tilde{Z}_{O_j} = \frac{z_{O_j} - z_{j_{min}}}{z_{j_{max}} - z_{j_{min}}}$$

where j denotes the index of an agricultural characteristic and s denotes the index of a candidate sampling location in the management zone S, where $z_{j_{max}}$ denotes the global maximum and $z_{j_{min}}$ denotes the global minimum for the jth agricultural characteristic, where $z_{S_j}$ denotes the value of the jth agricultural characteristic for the sth candidate sampling location and $z_{O_j}$ denotes the model value of the jth agricultural characteristic used by the agricultural modeling tool.

In some embodiments, the server is programmed to further weight values of the different agricultural characteristics. The weights for the different agricultural characteristics can be predetermined constants or received as input data. For example, the weights can reflect relative sensitivities or other significance values of the agricultural characteristics so that a larger weight for an agricultural characteristic would require a smaller difference between that agricultural characteristic value for a candidate sampling location and the corresponding model value used by the agricultural modeling tool in order for the candidate sampling location to be selected.

5.2 Selecting Sampling Locations

In some embodiments, the server is then configured to select a candidate sampling location u for each management zone (e.g., section) that minimizes the following distance metric:

$$u \equiv \underset{s \in S}{\operatorname{argmin}} \sum_j w_j |\tilde{z}_{s_j} - \tilde{z}_{O_j}|$$

In some embodiments, each component of the sum above can be the absolute value of the difference between $\tilde{z}_{s_j} - \tilde{z}_{O_j}$ or the square of that difference. Other distance metrics known to someone skilled in the art can be used. A customized distance function, which may incorporate the normalizing or weighting discussed above or a variant thereof, can also be used. For example, some agricultural characteristics may be correlated, and the customized distance function may include dynamic weights that depend on the strength of the correlations of an agricultural characteristic with other agricultural characteristics included in the comparison.

In some embodiments, when more than one candidate sampling location minimizes the distance metric for a management zone, the server can then be programmed to apply additional criteria to choose one from the more than one candidate sampling location. Example additional criteria or constraints include having a minimum distance to the boundary of the management zone or having an agricultural characteristic value in a specific range. These additional criteria or constraints can also be applied earlier to filter candidate sampling locations upfront. The server can also be configured to reevaluate the distance metric with adjusted weights for the more than one candidate sampling location.

In some embodiments, the server is configured to transmit data regarding the selected sampling locations to a display device or a remote client device. For each selected sampling location, the data can include the geographic coordinate (e.g., longitude and latitude), index of the enclosing management zone, distance from the boundary of the enclosing management zone, the corresponding set of agricultural characteristic values, or the corresponding value of the distance metric.

5.3 Alternative Process of Selecting a Sampling Location

In some embodiments, the server is programmed to receive input data including one or more of the following: a set of agricultural characteristics with their global ranges, a map for the management zone (e.g., section) indicating one or more values of the set of agricultural characteristics for each of a plurality of locations in the management zone, or a set of model values of the set of agricultural characteristics used by an agricultural modeling tool. The input data can also include a desired outcome, a buffer width for the management zone, or a minimum distance between adjacent sampling points.

In some embodiments, server can be programmed to generate field data or model data. Specifically, the server can be configured to define sampling units that are subject to various distance constraints, such as having any two sampling points separated by a minimum distance or having no sampling points within a minimum distance from the boundary of the management zone. The server can also be configured to expand the set of agricultural characteristic values included in the given map through duplication, interpolation, extrapolation, imputation, or other techniques to increase the number of candidate sampling locations as well as the number of agricultural characteristic values for each candidate sampling location. In addition, with the updated map, the server can be configured to feed the agricultural modeling tool new model values for the agricultural characteristics and receive new modeling results.

In some embodiments, the server is programmed to normalize or weight the agricultural characteristic values to eliminate issues caused by different measuring units while allowing flexibility in the treatment of different agricultural characteristics. The normalization can be done based on the global ranges of the agricultural characteristics. The weighting can be done based on relative sensitivities or other relevant significance values of the agricultural characteristics.

In some embodiments, the server is programmed to then select one of the candidate sampling locations in the management zone based on the normalized and weighted values. The server is configured to first identify those candidate sampling locations that minimize a distance metric measuring the distance between the values for the agricultural characteristics at these candidate sampling locations and the model values for the agricultural characteristics. The distance metric can include a sum of weighted absolute differences or squared differences over all the agricultural characteristics. The distance metric can also comprise another distance function known to someone skilled in the art.

In some embodiments, when multiple candidate sampling locations minimize the distance metric, the server can be configured to report all these candidate sampling locations. Alternatively, the server is configured to then select one of the multiple sampling locations having the smallest distance to the boundary of the management zone. Other criteria or constraints can be used to narrow down the list of candidate sampling locations, such as having a smallest distance to one specific side of the management zone or having an agricultural characteristic value in a particular range.

In some embodiments, the server is programmed to transmit results of the sampling location to a display device, a remote client device, or a remote server that maintains the agricultural modeling tool. The results can include, for each selected sampling location, the geographic coordinate, the index of the enclosing management zone, the distance to the boundary of the enclosing management zone, the set of agricultural characteristic values, the difference from the model values, or the modeling result.

5.4. Management Zones Identifying Management Zones Based on Yield Maps, Soil Maps, Topography Maps and Satellite Data In the context of precision agriculture, management zones are contiguous sub regions within an agricultural field that have similar constraints or limiting factors that influence harvested yields of crops. The field regions that belong to the same management zone can usually be managed uniformly in terms of seeding schedules or management practices. Identifying management zones within a field may help growers to make customized management decisions, such as choosing seed hybrids and seeding population that are best for each individual zone.

One objective for creating zones is to divide the entire agricultural field into different productivity regions having distinctive spatial-temporal yield behaviors. Creating, or identifying, such zones may help guiding growers to improve agricultural practices. This may include providing growers with recommendations for seeding rate selection, seeding timing, fertilizer selection and fertilizing timing for individual zones.

Recommendations that are customized to the needs of individual zones to improve yield and profitability of the field may include prescriptions for seeding, using certain seed hybrids, seed population and nitrogen fertilizer for different sub regions in a field. The recommendations may be determined based on characteristics of regions within a zone.

One criterion that may be used to determine the quality of management zones is compactness. Zones that are generated using a good management zone delineation approach are usually compact. Generating compact zones involves maximizing homogeneity within zones. There should also be a well-defined separation between different zones to ensure that the created zones actually require different management practices. The compactness and separation of the management zones that have been created may be evaluated by a visual assessment by either directly overlapping the delineated zones with yield maps, or by plotting a distribution of yield values in each zone and year, using appropriately programmed computers. The compactness and separation may also be evaluated by a quantitative assessment which defines numeric measures to accurately quantify the compactness and separation of yield observations in the delineated zones.

Management zones may be created automatically via computer programs, based on transient and permanent characteristics of an agricultural field. Transient characteristics may include yield data collected for sub regions and using historical yield maps. Permanent characteristics may include soil measurements and topographical properties of the field. The permanent characteristics data may be obtained from SSURGO maps and satellite images of the field. Permanent characteristics may be particularly useful when historical yield maps are unavailable for the field. Using the permanent characteristics of the field in determining management zones allows to incorporate to the zone creation process the data layers, such as soil and elevation data, in addition to yield data, and thus to refine the zone creation process.

Management zones that are created based on yield maps may group the regions with similar yield patterns and permanent properties. Such management zones aim to explain the productivity characteristics using the underlying properties of the soil. For example, zones with low organic matter or high pH may both have the low yield.

In an embodiment, a process of creating management zones comprises obtaining and processing transient characteristics data and permanent characteristics data for a field. The process may include determining desired sizes of the zones, and an optimal count of zones to achieve the desired productivity and yield from the field. The process may include creating one or more management zone delineation options, and separate planting plans for the individual options.

In an embodiment, a process of creating management zones comprises an interactive computer tool that is programmed for visualizing graphical representations of management zone delineation options and corresponding planting plans. The interactive tool may also be configured to manipulate layouts of the zones in the zone delineated options.

Graphical representations of management zones and planting plans may be generated using a GUI, and may graphically represent layouts of the zones, information about the zones, and planting plans for the zones.

5.4.1. Transient Feature Data—Yield Data

Transient feature data represents land or field characteristics that vary from time to time. In the context of agricultural management zones, examples of transient feature data may include yield data because the yields from a field vary from one harvesting season to another.

Yield data may include historical yield maps that represent spatial and temporal yield patterns for the sub-fields. Yield data may include information about yields of crops harvested from an agricultural field within one year or within several years. Yield data may also include additional information such as a field boundary, a field size, and a location of each sub-field within the field. Yield data may be provided from different sources. Examples of the sources may include research partners, agricultural agencies, agricultural organizations, growers, governmental agencies, and others.

5.4.2. Permanent Feature Data

Permanent feature data represents characteristics that remain unchanged from one season to another. In the context of agricultural management zones, examples of permanent feature data for a field may include characteristics of soil, topology and terrain of the field because such data usually does not change from one harvesting season to another.

Permanent feature data may include soil characteristics and topology characteristics. They may be obtained from soil survey maps, satellite maps, and baresoil maps. Permanent feature data may be provided as datasets. Examples of datasets include and Research Partner soil sampling datasets, Rapid-Eye images, SSURGO polygon boundaries and National Elevation Dataset (NED).

5.4.3. Soil Characteristics

Data for soil characteristics of a field may be obtained based on soil samples collected from the field. Soil sampling for a field may be performed using various sampling techniques, such as collecting soil samples at an approximate resolution of one sample per two acres. The samples are may be collected at grid points within a field and roughly form a rectangle. The original measurement data may be available as shape files stored on computer servers.

When soil samples are provided from different sources, there might be some differences in soil sampling methods, accuracy with which the samples were collected, and sampling depths at which the soil was sampled. Therefore, the datasets may be preprocessed. The preprocessing may include removing duplicated samples, samples with no associated values, samples with no geographical coordinate information, and samples with incorrect coordinates and geographical information.

5.4.4. Topology Characteristics

Topology characteristics of a field may include geographical and elevation characteristics of the field. Topology characteristics may include elevation data for an agricultural field, and other topographical properties that may be derived from the elevation data. The properties may include a wetness index, also referred to as a Composite Topographic Index CTI, a Topographic Position Index (TPI) indicator, an aspect, a flow direction, and a slope.

Elevation data may be obtained from different sources, including the National Elevation Dataset (NED). The NED dataset usually provides a resolution of about a third of an arc-second.

5.4.5. Soil Survey Maps

Soil survey characteristics may be provided in form of soil survey maps. One source of the soil survey maps is the SSURGO database that contains soil survey data of most areas in the United States.

A typical soil survey dataset is organized as a set of individual map units, each of which covers a polygon area. The data associated with each polygon may include soil properties and soil texture data, and the data may be provided at different spatial resolutions. The data may or may not be associated with specific geographical point locations.

Soil survey data may represent qualitative assessment and lab-analyzed sample data. Since the SSURGO maps provide a high resolution of soil measurement data, the soil texture data available in the SSURGO maps may be sufficient for the purpose of a zone creation. In a particular implementation, the applicable soil texture data is at mukey (a map unit key) level 2. That means that the value of soil texture properties is uniform over the entire spatial polygon.

In an embodiment, the SSURGO data for a set of fields of interest is provided as a set of spatial polygons. The set of polygons may be processed by for example, determining whether the soil texture data was missing for an entire polygon, and if so, a k-Nearest Neighbor (kNN) data points may be used to interpolate the missing data point. Furthermore, the sand, silt and clay percentages may be normalized to add up to a 100%. Examples of attributes used in a zone creation process include sand and silt attributes.

5.4.6. Satellite Maps

Satellite characteristics for an agricultural field are typically determined based on satellite maps. Satellite image data may be provided at different spatial, spectral and temporal resolutions. The satellite maps may provide information about agricultural crop assessment, crop health, change detection, environmental analysis, irrigated landscape mapping, yield determination and soils analysis. The images may be acquired at different times of the year and multiple times within a year.

Satellite images may depict variations in organic matter and drainage patterns. Soils higher in organic matter can be differentiated from lighter sandier soil that has a lower organic matter content. This information may be used in conjunction with other types of maps to define management zones for a field.

5.4.7. Baresoil Maps as Examples of Satellite Maps

Baresoil maps are examples of satellite maps. Baresoil maps include baresoil characteristics determined based on baresoil maps. Examples of such maps may include RapidEye satellite images. In a typical RapidEye image for a field, data may contain per-pixel (5 by 5 meter) percentage reflectance values for five different bands: red, red edge, blue, green, and near infra-red. Since the RapidEye data represents topsoil better than deeper soil layers, and that in the RP fields soil samples' depths may be unknown, using the RapidEye images may provide additional characteristics of the soil.

In an embodiment, a set of baresoil images is preprocessed. For example, for each field, the images with cloud contaminations may be discarded while the images from the most recent year may be selected.

5.5. Pipeline for Creating Management Zones

An objective for creating management zones is to divide an entire agricultural field into different productivity regions with distinctive spatial-temporal yielding behaviors. Creating, or identifying, such zones may help and guide the crops growers by providing the growers with recommendations for agricultural practices tailored for individual zones.

In an embodiment, management zones are delineated within an agricultural field using a management zone creating pipeline.

The process may receive program instructions for storing data representing transient and permanent characteristics of an agricultural field. The data may be stored at various data repositories, including server computers, databases, cloud storage systems, service providers, external data storage devices, and the like. Transient characteristics data may include yield data. Permanent characteristics data may be provided as soil maps, soil survey maps, topology maps, baresoil maps, and satellite images. Other information pertaining to the persistent characteristics of the soil and field may also be used.

The process may receive program instructions for receiving data. The data is received; for example, system receives yield data and permanent characteristics data as part of the field data. The data may include historical yield maps at the field level or sub field level, and maps representing persistent characteristics of the soil. The maps represent spatial-temporal patterns for the sub-fields and are used to classify a field into regions with distinctive or different productivity potentials.

Data may be received from different sources such as research partners (RP), agencies, organizations, growers and others. Received data may include information about yield of crops harvested from an agricultural field within one year or multiple years. In an embodiment, yield data may also include metadata such as a field boundary, a field size, and a location of each sub-field within the field.

5.5.1. Preprocessing

The process may receive program instructions for preprocessing, density processing and data smoothing of the received yield data. The process may be executed selectively, optionally, sequentially, or in parallel. The manner in which the tasks are performed can vary based on the implementation and the quality of received yield data. For example, some of the received data may need preprocessing but not smoothing. Other data may need only density processing.

Preprocessing may comprise programmatically identifying and removing data items that are outliers, invalid, redundant, or collected outside of a field boundary. Preprocessing may also include identifying, and removing, the yield observations if multiple crops were planted within the field in the same season.

The process may receive program instructions for preprocessing received data. Preprocessing may be performed, for example, because some of the data observations for a field were collected outside of corresponding field boundaries. The preprocessing may also be recommended when the data is provided from a field on which multiple crops were planted in the same season.

Preprocessing of the yield data may be performed to reduce noise observations from the yield observations, impute missing yield values to standardize the zone delineation step, and so forth. In an embodiment, received yield data is preprocessed to correct certain issues with the data. The preprocessing may include various types of data cleaning and filtering.

Preprocessing of yield data may include removing outliers from the yield data. Yield data may include sub-field yield observations that consist of various contaminations caused by unavoidable errors introduced by the way the crops are harvested, or by the way the yield data is collected or recorded. Removing of such errors or outliers effectively results in decontaminating the yield data.

In an embodiment, received yield data is analyzed to determine whether less than two years of yield maps for a field are provided. If less than two years of yield maps for a field are provided, then the yield maps are not included in the zone delineation.

Additional preprocessing and filtering of the data may be performed on yield data. An example is adjusting to account for grain moisture. Grain moisture adjustment allows correcting the yield data records for some fields and years that were harvested at a moisture level that is other than a standard moisture level such as 15.5% moisture.

Additional processing may be directed to correcting yield productivity data caused when the experimental yield data is provided. The additional processing may include correcting of yield data if the data was pre-smoothed by the data provider using undesired algorithms or parameters. This type of additional processing is recommended to reduce the effect of improperly smoothed yield data on the results of the management zones creation.

Additional preprocessing of the data may include transforming the data from latitude-longitude coordinates to Universal Transverse Mercator (UTM) coordinates, and mapping onto a grid that has been defined for the field. A 10 m×10 m grid has been used in one embodiment. The mapping allows standardization of locations of the yield records within the field.

Preprocessing of permanent characteristics data may include adjusting the soil samples to the resolution of samples per acre that was reported in the longitude and latitude coordinate system if the received data was sampled in a different resolution, and programmatically projecting the soil samples data onto UTM coordinates. Missing sample values may be interpolated at the UTM coordinates from the available data using a Gaussian process model with a constant trend whose parameters are obtained with maximum likelihood estimation.

Elevation, CTI and slope data of the yield data may be obtained directly from maps or from property raster data. This may include extracting cell values of the elevation raster where a yield spatial point falls in. If no cell raster is found, then an indication of no values is returned.

After a projection of the coordinates of a spatial polygon to UTM coordinates is performed, the SSURGO polygons may be overplayed to the spatial locations of the yield data.

In projecting the image data onto the UTM coordinate system, values of the image data at the location points of the yield data may be obtained by rasterizing the yield data and the results may be transferred to the yield raster cells. If one cell of yield data is covered by multiple imagery bands' data points, then an arithmetic mean of the values may be used to associate with the raster cell.

The process may receive program instructions for density processing of received data. Data density processing may be performed to normalize the yield data across different crops and fields. In an embodiment, data density processing comprises using an empirical cumulative distribution function (ECDF) transformation, which may be performed on the yield records for each field and year so that the transformed yield data is within a certain range across different crops and fields. For example, the ECDF may be applied to the received yield data to transform the data into transformed yield data in the range of [0, 1]. Once the yield data is transformed, the transformed yield data may be compared across different years and crops, such as corn, soy, or wheat.

5.5.2. Spatial Smoothing

Spatial smoothing is performed to remove measurement noises in raw yield observations and reduce unnecessary fragmentation of delineated management zones and may be performed using approaches such as a kernel-smoother, or a stationary Gaussian process. Data smoothing may be performed on either raw data or processed data depending on the quality of the received raw data.

A kernel smoother is a statistical technique for estimating a function by using its noise observations when no parametric model for the function is known. The resulting estimated function is usually smooth and may be used to remove the noise observations from a set of observations, such as the yield data. In an embodiment, kernel smoothers that are reliable and useful nonparametric estimators are selected to perform the spatial smoothing of the yield data. Examples of kernel smoothers that can be used to smooth the yield data include: Gaussian kernel, inverse distance weighting kernel, rectangular kernel, triangular kernel, bi-square kernel, tri-cube kernel, tri-weight kernel, etc. Besides their standard parameterization, all of them have a scale parameter h and a span parameter H such that the distance between yield data observations may be scaled and the observations that are more than H away from the destination point may be omitted in the smoothing process.

In some embodiments, the process may receive program instructions for smoothing received data. Data smoothing may include testing whether any yield data records are missing, whether the yield data records need to be further smoothed, or whether certain yield data records need to be removed or interpolated.

5.5.3. Normalization

In an embodiment, received data is normalized by transformation to a particular data range and the management zone delineation process may include using programmed instructions to transform yield data to generate transformed yield data. Transforming the yield data may comprise applying an empirical cumulative density function (ECDF) to the yield data to normalize the data to a certain range, such as a range of [0, 1]. The transformed yield data may be comparable across different years and types of crops. For example, the ECDF may allow transforming, or normalizing, yield records for each field and year, regardless of the crop type and the collection time, to a range of [0, 1], so that the transformed data may be comparable with each other.

ECDF transformation may be used to transform the yield data into the transformed yield data. Application of ECDF to the yield data may cause transforming the yield data records to transformed yield data records, each of which falls within a particular range. Applying ECDF to the yield data causes normalizing the yield data so that the normalized yield data is comparable across different years and crops, such as corn, soy, and wheat.

5.5.4. Clustering

Clustering is performed on data representing transient and permanent characteristic of an agricultural field to determine a plurality of cluster labels associated with pixels represented by the preprocessed data. In an embodiment, k-means clustering may be used. In the final step, zones with smaller sizes than s, which is set by configuration data or input, are merged into their most similar large neighboring zones.

Preprocessed data representing transient and permanent characteristic of an agricultural field is used to delineate a set of management zones for an agricultural field. The set of delineated management zones may be represented using stored digital zone data, and created by applying centroid-based approaches, such as the K-means approach, or a fuzzy C-means approach. The process may be repeated, one or more times until the quality of the created management zones is satisfactory. The process may be repeated using different criteria, different parameters, or different parameter values.

To address the goal of compactness that was previously discussed, a set of delineated management zones is analyzed to determine whether some of the zones may be merged. For example, a set of delineated management zones may be analyzed to identify small zones and to determine whether the small zones may be merged with neighboring larger zones. Small zones may be identified automatically by a computer system, or manually by a user of the computer system. For example, the computer system may display information about the set of first management zones to a crop grower in a graphical user interface that is programmed with widgets or controls to allow the grower to remove undesirable fragmented small zones, or to merge the fragmented small zones with larger zones. Merging of zones results in obtaining a set of merged management zones. If small zones cannot be identified in a set of delineated management zones, then the set of delineated management zones is provided.

The process may be repeated one or more times until no small zones are identified in the set of management zones. The process may be repeated using different criteria, different parameters, or different parameter values.

A set of management zones is post-processed. Post-processing of the management zones may include eliminating the zones that are fragmented or unusable.

The process may be repeated one or more times until the quality of created management zones is satisfactory. The process may be repeated using different criteria, different parameters, or different parameter values.

In an embodiment, metadata about the created management zones is stored. Furthermore, a test may be performed to determine whether the process of delineating management zones needs to be repeated. If the delineation process is to be repeated, then the delineating of the management zones is repeated.

What is claimed is:

1. A computer-implemented method of tracking soil sampling in a field, comprising:
   receiving digitally stored field map data from a first data storage source and digitally stored historical sampling data from a second data storage source, wherein the historical sampling data is indicative of at least one soil physical characteristic;
   based on the field map data and the historical sampling data, in a computer-generated graphical user interface, displaying a graphical map of an agricultural field comprising a first set of sampling points, each sampling point of the first set of sampling points being assigned to a corresponding section in the field map that is associated with a corresponding geographic coordinate;
   receiving a selection of a first sampling point of the first set of sampling points;
   displaying, in the computer-generated graphical user interface, first sampling data that is associated with the first sampling point, the first sampling data comprising a set of soil physical characteristics and a set of order data of the first sampling data, the set of soil physical characteristics including at least one of a pH level, acidity, macronutrients, and/or micronutrients, and the set of order data of the first sampling data including at least one of a sampled date, a shipment date, a collector identification, and/or a sampling protocol;
   receiving an update to the set of order data, the update indicating that a soil sample has been collected at the first sampling point;
   based on the received update:
      retrieving laboratory data identifying one or more available testing facilities that are capable of testing the soil sample, the laboratory data being linked to the field map;
      displaying, in the computer-generated graphical user interface, the one or more available testing facilities;
      receiving a selection of a particular testing facility from among the one or more available testing facilities via the computer-generated graphical user interface;
      transmitting the updated set of order data of the first sampling data to a computer of the selected testing facility over a network; and
      highlighting, in the field map, the first sampling point to visually depict the first sampling point differently from other ones of the first set of sampling points;
   determining a second sampling point at which a next soil sample is to be collected based on a sampling protocol; and
   displaying the second sampling point in the field map, the second sampling point being depicted using visually different attributes compared to the first sampling point;
   wherein the method is performed using one or more computing devices.

2. The computer-implemented method of claim 1, wherein the first sampling data further comprises a topological characteristic.

3. The computer-implemented method of claim 1, wherein the field map indicates geographic coordinates of one or more sections, a distance to a boundary of the one or more sections, or the historical sampling data for the one or more sections.

4. The computer-implemented method of claim 1, further comprising:
   transmitting the updated set of order data of the first sampling data to a peripheral computing device, the peripheral computing device being programmed to print a tag based on the order data of the first sampling data, the tag being capable of affixation to the collected soil sample.

5. The computer-implemented method of claim 1, further comprising:
   receiving input to assign a second set of sampling points to one or more sections in the field map, the second set of sampling points having second geographic coordinates that are different from geographic coordinates of the first set of sampling points in the field map;
   renumbering the second set of sampling points according to the second geographic coordinates; and
   in the field map, visually replacing the first set of sampling points with the second set of sampling points.

6. The computer-implemented method of claim 1, further comprising:
   receiving a geographic coordinate of a computing device via a Global Positioning System (GPS) tracking information associated with the computing device;
   identifying a section associated with the received geographic coordinate in the field map; and
   displaying a third sampling point associated with the identified section in the field map.

7. The computer-implemented method of claim 1, wherein the soil sampling comprises at least one of tissue sampling or phenology sampling.

8. One or more non-transitory storage media storing instructions which, when executed by one or more computing devices, cause performance of a method of tracking soil sampling in a field, the method comprising:
   receiving digitally stored field map data from a first data storage source and digitally stored historical sampling data from a second data storage source, wherein the historical sampling data is indicative of at least one soil physical characteristic;
   based on the field map data and the historical sampling data, in a computer-generated graphical user interface, displaying a graphical map of an agricultural field comprising a first set of sampling points, each sampling point of the first set of sampling points being assigned to a corresponding section in the field map that is associated with a corresponding geographic coordinate;
   receiving a selection of a first sampling point of the first set of sampling points;
   displaying, in the computer-generated graphical user interface, first sampling data that is associated with the first sampling point, the first sampling data comprising a set of soil physical characteristics and a set of order data of the first sampling data, the set of soil physical characteristics including at least one of a pH level, acidity, macronutrients, and/or micronutrients, and the set of order data of the first sampling data including at least one of a sampled date, a shipment date, a collector identification, and/or a sampling protocol;

receiving an update to the set of order data, the update indicating that a soil sample has been collected at the first sampling point;

based on the received update:
retrieving laboratory data identifying one or more available testing facilities that are capable of testing the soil sample, the laboratory data being linked to the field map;
displaying, in the computer-generated graphical user interface, the one or more available testing facilities;
receiving a selection of a particular testing facility from among the one or more available testing facilities via the computer-generated graphical user interface;
transmitting the updated set of order data of the first sampling data to a computer of the selected testing facility over a network; and
highlighting, in the field map, the first sampling point to visually depict the first sampling point differently from other ones of the first set of sampling points;
determining a second sampling point at which a next soil sample is to be collected based on a sampling protocol; and
displaying the second sampling point in the field map, the second sampling point being depicted using visually different attributes compared to the first sampling point.

9. The one or more non-transitory storage media of claim 8, wherein the first sampling data further comprises a topological characteristic.

10. The one or more non-transitory storage media of claim 8, wherein the field map indicates geographic coordinates of one or more sections, a distance to a boundary of the one or more sections, or the historical sampling data for the one or more sections.

11. The one or more non-transitory storage media of claim 8, the method further comprising:
transmitting the updated set of order data of the first sampling data to a peripheral computing device, the peripheral computing device being programmed to print a tag based on the order data of the first sampling data, the tag being capable of affixation to the collected soil sample.

12. The one or more non-transitory storage media of claim 8, the method further comprising:
receiving input to assign a second set of sampling points to one or more sections in the field map, the second set of sampling points having second geographic coordinates that are different from geographic coordinates of the first set of sampling points in the field map;
renumbering the second set of sampling points according to the second geographic coordinates; and
in the field map, visually replacing the first set of sampling points with the second set of sampling points.

13. The one or more non-transitory storage media of claim 8, the method further comprising:
receiving a geographic coordinate of a computing device via a Global Positioning System (GPS) tracking information associated with the computing device;
identifying a section associated with the received geographic coordinate in the field map; and
displaying a third sampling point associated with the identified section in the field map.

14. The one or more non-transitory storage media of claim 8, wherein the soil sampling comprises at least one of tissue sampling or phenology sampling.

15. A data processing system comprising:
a memory; and
one or more processors coupled to the memory and programmed to:
receive digitally stored field map data from a first data storage source and digitally stored historical sampling data from a second data storage source, wherein the historical sampling data is indicative of at least one soil physical characteristic;
based on the field map data and the historical sampling data, in a computer-generated graphical user interface, display a graphical map of an agricultural field comprising a first set of sampling points, each sampling point of the first set of sampling points being assigned to a corresponding section in the field map that is associated with a corresponding geographic coordinate;
receive a selection of a first sampling point of the first set of sampling points;
display, in the computer-generated graphical user interface, first sampling data that is associated with the first sampling point, the first sampling data comprising a set of soil physical characteristics and a set of order data of the first set of sampling data, the set of soil physical characteristics including at least one of a pH level, acidity, macronutrients, and/or micronutrients, and the set of order data of the first sampling data including at least one of a sampled date, a shipment date, a collector identification, and/or a sampling protocol;
receive an update to the set of order data, the update indicating that a soil sample has been collected at the first sampling point;
based on the received update:
retrieve laboratory data identifying one or more available testing facilities that are capable of testing the soil sample, the laboratory data being linked to the field map;
display, in the computer-generated graphical user interface, the one or more available testing facilities;
receive a selection of a particular testing facility from among the one or more available testing facilities via the computer-generated graphical user interface;
transmit the updated set of order data of the first sampling data to a computer of the selected testing facility over a network; and
highlight, in the field map, the first sampling point to visually depict the first sampling point differently from other ones of the first set of sampling points;
determine a second sampling point at which a next soil sample is to be collected based on a sampling protocol; and
display the second sampling point in the field map, the second sampling point being depicted using visually different attributes compared to the first sampling point.

16. The data processing system of claim 15, wherein the soil sampling comprises at least one of tissue sampling or phenology sampling.

* * * * *